(12) United States Patent
Bath et al.

(10) Patent No.: US 11,033,698 B2
(45) Date of Patent: *Jun. 15, 2021

(54) WIRE HEATED TUBE WITH TEMPERATURE CONTROL SYSTEM, TUBE TYPE DETECTION, AND ACTIVE OVER TEMPERATURE PROTECTION FOR HUMIDIFIER FOR RESPIRATORY APPARATUS

(71) Applicant: ResMed Pty Ltd, Bella Vista (AU)

(72) Inventors: Andrew Roderick Bath, Sydney (AU); Donald Angus Richmond, Sydney (AU); Nathan John Row, Sydney (AU); Jianhua Zhu, Sydney (AU); Timothy Nicholas Shadie, Sydney (AU); Ronald James Huby, Sydney (AU); Ivan Teodor Dujmovic, Sydney (AU)

(73) Assignee: ResMed Pty Ltd, Bella Vista (AU)

( * ) Notice: Subject to any disclaimer, the term of this patent is extended or adjusted under 35 U.S.C. 154(b) by 161 days.

This patent is subject to a terminal disclaimer.

(21) Appl. No.: 16/106,191

(22) Filed: Aug. 21, 2018

(65) Prior Publication Data

US 2019/0001091 A1   Jan. 3, 2019

Related U.S. Application Data

(63) Continuation of application No. 14/219,036, filed on Mar. 19, 2014, now Pat. No. 10,086,158, which is a
(Continued)

(51) Int. Cl.
*A61M 16/00* (2006.01)
*A61M 16/08* (2006.01)
(Continued)

(52) U.S. Cl.
CPC .... *A61M 16/0051* (2013.01); *A61M 16/0003* (2014.02); *A61M 16/0066* (2013.01);
(Continued)

(58) Field of Classification Search
CPC .......... A61M 16/0003; A61M 16/0051; A61M 16/0069; A61M 16/024; A61M 16/0875; A61M 16/1075; A61M 16/16
See application file for complete search history.

(56) References Cited

U.S. PATENT DOCUMENTS

| 1,085,833 A | 2/1914 | Wilson |
| 2,073,335 A | 3/1937 | Connell |

(Continued)

FOREIGN PATENT DOCUMENTS

| AU | 14863/95 | 9/1995 |
| AU | 2010206053 | 2/2011 |

(Continued)

OTHER PUBLICATIONS

Further Examination Report dated May 14, 2018 issued in New Zealand Application No. 723393 (2 pages).
(Continued)

*Primary Examiner* — Kathryn E Ditmer
(74) *Attorney, Agent, or Firm* — Nixon & Vanderhye P.C.

(57) ABSTRACT

A flow generator includes a blower, a flow generator outlet configured to receive an end of a gas delivery tube, and a controller. The flow generator outlet includes electrical connectors configured to contact corresponding electrical connectors associated with the breathable gas delivery tube when the breathable gas delivery tube is received by the flow generator outlet. The controller includes a tube-type detect circuit and is configured to receive signals from the breathable gas delivery tube by way of the electrical connectors of the flow generator outlet. The tube-type detect circuit is
(Continued)

configured so that when the breathable gas delivery tube is received by the flow generator outlet, the tube-type detect circuit determines the type of breathable gas delivery tube based on signals from the electrical connectors of the flow generator outlet that are indicative of a condition of a resistor associated with the breathable gas delivery tube.

20 Claims, 26 Drawing Sheets

Related U.S. Application Data continuation of application No. 12/847,021, filed on Jul. 30, 2010, now Pat. No. 8,733,349.

(60) Provisional application No. 61/334,761, filed on May 14, 2010, provisional application No. 61/230,128, filed on Jul. 31, 2009.

(51) Int. Cl.
  *A61M 16/16* (2006.01)
  *A61M 16/06* (2006.01)
  *A61M 16/10* (2006.01)

(52) U.S. Cl.
  CPC ...... *A61M 16/0069* (2014.02); *A61M 16/024* (2017.08); *A61M 16/06* (2013.01); *A61M 16/065* (2014.02); *A61M 16/0816* (2013.01); *A61M 16/0875* (2013.01); *A61M 16/109* (2014.02); *A61M 16/1075* (2013.01); *A61M 16/1095* (2014.02); *A61M 16/16* (2013.01); *A61M 16/161* (2014.02); *A61M 16/0605* (2014.02); *A61M 2016/0021* (2013.01); *A61M 2016/0027* (2013.01); *A61M 2016/0039* (2013.01); *A61M 2205/051* (2013.01); *A61M 2205/18* (2013.01); *A61M 2205/3306* (2013.01); *A61M 2205/3368* (2013.01); *A61M 2205/3375* (2013.01); *A61M 2205/42* (2013.01); *A61M 2205/502* (2013.01); *A61M 2205/581* (2013.01); *A61M 2205/582* (2013.01); *A61M 2205/584* (2013.01); *A61M 2230/205* (2013.01); *A61M 2230/62* (2013.01)

(56) References Cited

U.S. PATENT DOCUMENTS

| | | |
|---|---|---|
| 2,516,864 A | 8/1950 | Gilmore |
| 2,840,682 A | 6/1958 | Rubenstein |
| 2,875,314 A | 2/1959 | Schreyer |
| 3,584,192 A | 6/1971 | Maag |
| 3,659,604 A | 5/1972 | Melville et al. |
| 3,871,373 A | 3/1975 | Jackson |
| 3,982,095 A | 9/1976 | Robinson |
| 3,987,133 A | 10/1976 | Andra |
| 4,014,382 A | 3/1977 | Heath |
| 4,038,519 A | 7/1977 | Foucras |
| 4,038,980 A | 8/1977 | Fodor |
| 4,051,205 A | 9/1977 | Grant |
| 4,060,576 A | 11/1977 | Grant |
| 4,086,305 A | 4/1978 | Dobritz |
| 4,098,853 A * | 7/1978 | Brown .............. A61M 16/1075 128/200.13 |
| 4,110,419 A | 8/1978 | Miller |
| 4,146,597 A | 3/1979 | Eckstein et al. |
| 4,152,379 A | 5/1979 | Suhr |
| 4,155,961 A | 5/1979 | Benthin |
| 4,201,204 A | 5/1980 | Rinne et al. |
| 4,203,027 A | 5/1980 | O'Hare et al. |
| 4,322,594 A | 3/1982 | Brisson |
| 4,357,936 A | 11/1982 | Ellestad et al. |
| 4,367,734 A | 1/1983 | Benthin |
| 4,430,994 A | 2/1984 | Clawson et al. |
| 4,561,287 A | 2/1985 | Rowland |
| 4,532,088 A | 7/1985 | Miller |
| 4,564,748 A | 1/1986 | Gupton |
| 4,621,632 A | 11/1986 | Bartels et al. |
| 4,657,713 A | 4/1987 | Miller |
| 4,686,354 A | 8/1987 | Makin |
| 4,708,831 A | 11/1987 | Elsworth et al. |
| 4,714,078 A | 12/1987 | Paluch |
| 4,753,758 A | 6/1988 | Miller |
| 4,793,343 A * | 12/1988 | Cummins, Jr. ... A61M 16/1075 128/203.27 |
| 4,829,998 A | 5/1989 | Jackson |
| 4,861,523 A | 8/1989 | Beran |
| 4,865,777 A | 9/1989 | Weiler et al. |
| 4,891,171 A | 1/1990 | Weiler et al. |
| 4,910,384 A | 3/1990 | Silver |
| 4,913,140 A | 4/1990 | Orec et al. |
| 4,921,642 A | 5/1990 | LaTorraca |
| 5,031,612 A | 7/1991 | Clementi |
| 5,056,712 A | 10/1991 | Enck |
| 5,062,145 A | 10/1991 | Zwaan et al. |
| 5,092,326 A | 3/1992 | Winn et al. |
| 5,163,423 A | 11/1992 | Suzuki |
| 5,220,151 A | 6/1993 | Terayama |
| 5,230,331 A | 7/1993 | Rusz et al. |
| 5,231,979 A | 8/1993 | Rose et al. |
| 5,357,948 A | 10/1994 | Eilentropp |
| 5,367,146 A * | 11/1994 | Grunig .................. F24C 15/106 219/497 |
| 5,367,604 A | 11/1994 | Murray |
| 5,368,786 A | 11/1994 | Dinauer |
| 5,383,874 A * | 1/1995 | Jackson ................ A61B 18/00 606/1 |
| 5,392,770 A | 2/1995 | Clawson et al. |
| 5,411,052 A | 5/1995 | Murray |
| 5,429,123 A | 7/1995 | Shaffer et al. |
| 5,445,143 A | 8/1995 | Sims |
| 5,454,061 A | 9/1995 | Carlson |
| 5,468,961 A | 11/1995 | Gradon et al. |
| 5,529,060 A | 6/1996 | Salmon et al. |
| 5,537,996 A | 7/1996 | McPhee |
| 5,537,997 A | 7/1996 | Mechlenburg et al. |
| 5,558,084 A | 9/1996 | Daniell et al. |
| 5,564,415 A | 10/1996 | Dobson et al. |
| 5,588,423 A | 12/1996 | Smith |
| 5,598,837 A | 2/1997 | Sirianne, Jr. et al. |
| 5,640,951 A | 6/1997 | Huddart et al. |
| 5,655,522 A | 8/1997 | Mechlenburg et al. |
| 5,660,567 A * | 8/1997 | Nierlich ............. A61B 5/14551 439/620.21 |
| 5,673,687 A | 10/1997 | Dobson et al. |
| 5,694,923 A | 12/1997 | Hete et al. |
| 5,740,795 A | 4/1998 | Brydon |
| 5,769,071 A | 6/1998 | Turnbull |
| 5,800,741 A | 9/1998 | Glenn et al. |
| 5,916,493 A | 6/1999 | Miller |
| 5,937,855 A | 8/1999 | Zdrojkowski et al. |
| 5,947,115 A | 9/1999 | Lordo et al. |
| 5,988,164 A | 11/1999 | Paluch |
| 6,010,118 A | 1/2000 | Milewicz |
| 6,017,315 A | 1/2000 | Starr et al. |
| 6,050,260 A | 4/2000 | Daniell et al. |
| 6,050,552 A | 4/2000 | Loescher et al. |
| 6,078,730 A | 6/2000 | Huddart et al. |
| 6,095,135 A | 8/2000 | Clawson et al. |
| 6,095,505 A | 8/2000 | Miller |
| 6,102,037 A | 8/2000 | Koch |
| 6,116,029 A | 9/2000 | Krawec |
| 6,126,610 A * | 10/2000 | Rich ................ A61M 16/0816 600/529 |
| 6,135,432 A | 10/2000 | Hebblewhite et al. |
| 6,142,992 A * | 11/2000 | Cheng ................ A61B 18/1206 606/34 |
| 6,149,620 A * | 11/2000 | Baker ................ A61B 18/1402 604/22 |
| 6,157,244 A | 12/2000 | Lee et al. |
| 6,167,883 B1 | 1/2001 | Beran et al. |

(56) References Cited

U.S. PATENT DOCUMENTS

| | | |
|---|---|---|
| 6,201,223 B1 | 3/2001 | Nitta |
| 6,210,402 B1* | 4/2001 | Olsen .................. A61B 18/1482 606/32 |
| 6,219,490 B1 | 4/2001 | Gibertoni et al. |
| 6,272,933 B1 | 8/2001 | Gradon et al. |
| 6,335,517 B1 | 1/2002 | Chauviaux et al. |
| 6,338,473 B1 | 1/2002 | Hebblewhite et al. |
| 6,349,722 B1 | 2/2002 | Gradon et al. |
| 6,349,724 B1 | 2/2002 | Burton et al. |
| 6,363,930 B1 | 4/2002 | Clawson et al. |
| 6,367,472 B1 | 4/2002 | Koch |
| 6,394,084 B1 | 5/2002 | Nitta |
| 6,398,197 B1 | 6/2002 | Dickinson et al. |
| 6,435,180 B1 | 8/2002 | Hewson et al. |
| 6,437,316 B1 | 8/2002 | Colman et al. |
| 6,470,885 B1 | 10/2002 | Blue et al. |
| 6,510,848 B1 | 1/2003 | Gibertoni |
| 6,520,021 B1 | 2/2003 | Wixey et al. |
| 6,523,810 B2 | 2/2003 | Offir et al. |
| 6,554,260 B1 | 4/2003 | Lipscombe et al. |
| 6,557,551 B2 | 5/2003 | Nitta |
| 6,584,972 B2 | 7/2003 | McPhee |
| 6,592,107 B1 | 7/2003 | Wong |
| 6,598,604 B1 | 7/2003 | Seakins |
| 6,615,831 B1 | 9/2003 | Tuitt et al. |
| 6,629,934 B2 | 10/2003 | Mault et al. |
| 6,694,974 B1 | 2/2004 | George-Gradon et al. |
| 6,718,973 B2 | 4/2004 | Koch |
| 6,718,974 B1 | 4/2004 | Moberg |
| 6,772,999 B2 | 8/2004 | Lipscombe et al. |
| 6,802,314 B2 | 10/2004 | McPhee |
| 6,827,340 B2 | 12/2004 | Austin et al. |
| 6,877,510 B2 | 4/2005 | Nitta |
| 6,895,803 B2 | 5/2005 | Seakins et al. |
| 6,918,389 B2 | 7/2005 | Seakins et al. |
| 6,935,337 B2 | 8/2005 | Virr et al. |
| 6,953,354 B2 | 10/2005 | Edirisuriya et al. |
| 7,043,979 B2 | 5/2006 | Smith et al. |
| 7,073,500 B2 | 7/2006 | Kates |
| 7,086,399 B2 | 8/2006 | Makinson et al. |
| 7,111,624 B2 | 9/2006 | Thudor et al. |
| 7,140,367 B2 | 11/2006 | White et al. |
| 7,146,979 B2 | 12/2006 | Seakins et al. |
| 7,182,738 B2* | 2/2007 | Bonutti ................ A61F 5/0102 601/5 |
| 7,291,240 B2 | 11/2007 | Smith et al. |
| 7,306,205 B2 | 12/2007 | Huddart et al. |
| 7,413,173 B2 | 8/2008 | DiMatteo et al. |
| 7,478,635 B2 | 1/2009 | Wixey et al. |
| 7,677,246 B2 | 3/2010 | Kepler et al. |
| D628,288 S | 11/2010 | Row et al. |
| D629,891 S | 12/2010 | Virr et al. |
| 8,733,349 B2 | 5/2014 | Bath et al. |
| 9,572,949 B2 | 2/2017 | Vos |
| 2001/0029340 A1 | 10/2001 | Mault et al. |
| 2002/0112725 A1 | 8/2002 | Thudor et al. |
| 2003/0023135 A1* | 1/2003 | Ulmsten ................ A61B 5/7435 600/29 |
| 2003/0153833 A1* | 8/2003 | Bennett ................ B06B 1/0677 600/439 |
| 2003/0154977 A1 | 8/2003 | White et al. |
| 2003/0176856 A1* | 9/2003 | Howell ................ A61B 90/90 606/29 |
| 2003/0236015 A1* | 12/2003 | Edirisuriya .......... F16L 25/0036 439/191 |
| 2004/0010246 A1* | 1/2004 | Takahashi .............. G16H 40/63 606/1 |
| 2004/0045352 A1 | 3/2004 | Kamiunten |
| 2004/0074493 A1 | 4/2004 | Seakins et al. |
| 2004/0079370 A1 | 4/2004 | Gradon et al. |
| 2004/0081784 A1 | 4/2004 | Smith et al. |
| 2004/0102731 A1 | 5/2004 | Blackhurst et al. |
| 2004/0182386 A1 | 9/2004 | Meier |
| 2004/0182392 A1 | 9/2004 | Gerder et al. |
| 2004/0221844 A1* | 11/2004 | Hunt ................ A61M 16/0875 128/204.17 |
| 2005/0118048 A1* | 6/2005 | Traxinger ........... A61M 1/0058 417/477.2 |
| 2006/0001433 A1* | 1/2006 | Bouton ................ H02H 1/0015 324/536 |
| 2006/0037613 A1 | 2/2006 | Kwok et al. |
| 2006/0102175 A1* | 5/2006 | Nelson ................ A61M 11/042 128/200.24 |
| 2006/0113294 A1 | 6/2006 | Lomaglio |
| 2006/0113690 A1* | 6/2006 | Huddart ............. A61M 16/161 261/129 |
| 2006/0137445 A1 | 6/2006 | Smith et al. |
| 2006/0191531 A1 | 8/2006 | Mayer et al. |
| 2006/0213515 A1 | 9/2006 | Bremner et al. |
| 2006/0272639 A1 | 12/2006 | Makinson et al. |
| 2006/0278221 A1 | 12/2006 | Schermeier et al. |
| 2006/0283450 A1 | 12/2006 | Shissler |
| 2007/0061051 A1 | 3/2007 | Maddox |
| 2007/0079826 A1 | 4/2007 | Kramer et al. |
| 2007/0210462 A1 | 9/2007 | Felty et al. |
| 2007/0230927 A1 | 10/2007 | Kramer |
| 2007/0283957 A1 | 12/2007 | Schobel et al. |
| 2007/0284361 A1 | 12/2007 | Nadjafizadeh et al. |
| 2008/0028850 A1* | 2/2008 | Payton ................ A61M 16/161 73/204.19 |
| 2008/0072900 A1 | 3/2008 | Kenyon et al. |
| 2008/0078388 A1 | 4/2008 | Vandine |
| 2008/0105257 A1 | 5/2008 | Klasek |
| 2008/0257346 A1* | 10/2008 | Lathrop ............. A61M 16/0066 128/204.17 |
| 2008/0302361 A1 | 12/2008 | Snow et al. |
| 2009/0025723 A1 | 1/2009 | Schobel et al. |
| 2009/0107982 A1* | 4/2009 | McGhin ............. A61M 16/1095 219/497 |
| 2009/0184832 A1 | 7/2009 | Lloyd |
| 2009/0223514 A1 | 9/2009 | Smith et al. |
| 2009/0229606 A1* | 9/2009 | Tang ................ A61M 16/0057 128/203.14 |
| 2009/0320840 A1* | 12/2009 | Klasek ................ A61M 16/108 128/203.27 |
| 2010/0078030 A1* | 4/2010 | Colburn ............ A61M 16/0443 128/207.14 |
| 2010/0317961 A1* | 12/2010 | Jenkins ................ A61B 5/065 600/411 |
| 2011/0023874 A1 | 2/2011 | Bath et al. |
| 2011/0088693 A1* | 4/2011 | Somervell ........... A61M 16/161 128/203.14 |
| 2011/0162647 A1* | 7/2011 | Huby .................... A61M 16/16 128/203.14 |
| 2012/0074125 A1 | 3/2012 | Burkett |
| 2014/0216459 A1 | 1/2014 | Vos et al. |
| 2014/0202460 A1 | 7/2014 | Bath et al. |

FOREIGN PATENT DOCUMENTS

| | | |
|---|---|---|
| DE | 33 11 811 A1 | 10/1984 |
| DE | 36 29 353 C1 | 1/1988 |
| DE | 4020522 A1 * | 1/1992 .......... A61M 5/1456 |
| DE | 40 34 611 A1 | 5/1992 |
| DE | 94 09 231.1 U1 | 12/1994 |
| DE | 196 02 077 A | 8/1996 |
| DE | 299 09 611 U1 | 10/1999 |
| DE | 199 28 003 A | 12/2000 |
| DE | 200 18 593 U1 | 2/2001 |
| DE | 202 02 906 U1 | 6/2002 |
| DE | 10 2005 007 773 | 9/2005 |
| DE | 10 2007 003454 A1 | 7/2008 |
| EP | 0 097 901 A2 | 1/1984 |
| EP | 0 201 985 A1 | 11/1986 |
| EP | 0 258 928 A1 | 3/1988 |
| EP | 0 439 950 A1 | 8/1991 |
| EP | 1 005 878 A2 | 6/2000 |
| EP | 1 479 404 A2 | 11/2004 |
| EP | 1 514 570 A2 | 3/2005 |
| EP | 1 491 226 B1 | 1/2006 |
| EP | 1 197 237 B1 | 1/2007 |
| GB | 2 277 689 A | 11/1994 |

(56) References Cited

FOREIGN PATENT DOCUMENTS

| | | |
|---|---|---|
| GB | 2 293 325 A | 3/1996 |
| GB | 2 322 709 A | 9/1998 |
| GB | 2 338 420 A | 12/1999 |
| JP | 5-317428 A | 12/1993 |
| JP | H06 114003 A | 4/1994 |
| JP | 8-61731 A | 3/1996 |
| JP | 9-234247 A | 9/1997 |
| SU | 379270 | 4/1973 |
| WO | 95/32016 A1 | 11/1995 |
| WO | WO 97/47348 A1 | 12/1997 |
| WO | WO 98/04311 A1 | 2/1998 |
| WO | WO 00/21602 A1 | 4/2000 |
| WO | WO 01/13981 A1 | 3/2001 |
| WO | WO 01/56454 A2 | 8/2001 |
| WO | WO 03/055554 A1 | 7/2003 |
| WO | WO 2004/011072 A1 | 2/2004 |
| WO | WO 2004/039444 A1 | 5/2004 |
| WO | WO 2004/105848 A1 | 12/2004 |
| WO | WO 2005/011556 A2 | 2/2005 |
| WO | WO 2005/021076 A2 | 3/2005 |
| WO | WO 2005/079898 | 9/2005 |
| WO | WO 2005/079898 A2 | 9/2005 |
| WO | WO 2006/019323 A1 | 2/2006 |
| WO | WO-2006092001 A1 * | 9/2006 ........ A61M 16/0069 |
| WO | 2006/117591 A1 | 11/2006 |
| WO | 2007/101297 | 9/2007 |
| WO | 2008/025080 | 3/2008 |
| WO | WO 2008/055308 A1 | 5/2008 |
| WO | WO 2008/056993 A2 | 5/2008 |
| WO | WO 2008/148154 A1 | 12/2008 |
| WO | WO 2009/015410 A1 | 2/2009 |
| WO | WO 2009/022004 A2 | 2/2009 |
| WO | WO 2010/031126 A1 | 3/2010 |

OTHER PUBLICATIONS

First Examination Report dated Feb. 27, 2018 issued in New Zealand Application No. 739850 (2 pages).
Extended European Search Report dated Sep. 20, 2017 issued in European Application No. 17172468.5 (8 pages).
Further Examination Report dated Aug. 25, 2017 issued in New Zealand Application No. 723393 (2 pages).
Further Examination Report dated Dec. 5, 2016 issued in New Zealand Application No. 706816 (5 pages).
First Examination Report dated Sep. 8, 2016 issued in New Zealand Application No. 723393 (2 pages).
Patent Examination Report No. 3 dated Jun. 27, 2016 issued in Australian Application No. 2014250602 (3 pages).
Office Action dated Apr. 27, 2016 issued in U.S. Appl. No. 14/169,714 (18 pages).
Second Patent Examination Report dated Feb. 25, 2016 issued in Australian Application No. 2014250602 (6 pages).
First Examination Report dated Oct. 23, 2015 issued in Australian Application No. 2014250602 (10 pages).
First Examination Report dated Aug. 11, 2015 issued in related New Zealand Application No. 710078 (3 pages).
Second Examination Report dated Apr. 9, 2014 in Australian Application No. 2010206053 (3 pages).
Extended European Search Report dated Mar. 27, 2015 issued in European Application No. 14153460.2 (6 pages).
Wiest et al., "In Vivo Efficacy of Two Heated Humidifiers Used During CPAP-Therapy for Obstructive Sleep Apnea Under Various Environmental Conditions," Sleep, vol. 24., No. 4, 2001, Abstract.
Fairchild Semiconductor, "MM74HC74A Dual D-Type Flip-Flop with Preset and Clear," Sep. 1983 (Revised Jan. 2005), pp. 1-8.
TelCom Semiconductor, Inc., "3-Pin μP Reset Monitors," TCM809/810-04, Aug. 29, 1996, pp. 5-15 through 5-18.
Unitrode Products from Texas Instruments, "Current Mode PWM Controller," SLUS224A, Sep. 1994 (Revised Apr. 2002), 11 pages.
National Semiconductor Corporation, "LP339 Ultra-Low Power Quad Comparator," DS005226, Aug. 2000, pp. 1-12.
Examination Report dated Nov. 3, 2011 in New Zealand Application No. 596092 (2 pages).
Notice of Opposition to Grant to Patent dated Apr. 23, 2012 in New Zealand Appln. No. 587113 (3 pages).
New Zealand Examination Report dated Jul. 2, 2012 in New Zealand Application No. 596092 (2 pages).
New Zealand Examination Report dated Jul. 2, 2012 in New Zealand Application No. 600986 (2 pages).
Amended Notice of Opposition to Grant of Patent and Statement of Case mailed Sep. 21, 2012 in New Zealand Application No. 587113 (33 pages).
First Examination Report dated May 13, 2013 in New Zealand Application No. 610299.
Patent Examination Report No. 1 dated Oct. 18, 2013 in Australian Application No. 2010206053 (5 pages).
First Examination Report dated Dec. 6, 2019 issued in New Zealand Application No. 759342 (2 pages).
Extended European Search Report dated Dec. 23, 2020 issued in European Application No. 20177117.7 (7 pages).

* cited by examiner

WIRE HEATED TUBE WITH TEMPERATURE CONTROL SYSTEM, TUBE TYPE DETECTION, AND ACTIVE OVER TEMPERATURE PROTECTION FOR HUMIDIFIER FOR RESPIRATORY APPARATUS

CROSS REFERENCE TO RELATED APPLICATIONS

This application is a continuation of U.S. application Ser. No. 14/219,036, filed Mar. 19, 2014, which is a continuation of U.S. application Ser. No. 12/847,021, filed Jul. 30, 2010, now U.S. Pat. No. 8,733,349, which claims the benefit of U.S. Provisional Applications 61/230,128, filed Jul. 31, 2009, and 61/334,761, filed May 14, 2010, the entire contents of each of which are incorporated herein by reference.

The entire contents of each of WO 2010/031126 A1 and U.S. Patent Application Publications 2008/0105257 A1, 2009/0223514 A1, and 2010/0116272 A1 are incorporated herein by reference.

BACKGROUND OF THE INVENTION

1. Field of the Invention

The present technology relates to humidification and heater arrangements used to control the humidity of breathable gases used in all forms of respiratory apparatus ventilation systems including invasive and non-invasive ventilation, Continuous Positive Airway Pressure (CPAP), Bi-Level therapy and treatment for sleep disordered breathing (SDB) conditions such as Obstructive Sleep Apnea (OSA), and for various other respiratory disorders and diseases.

2. Description of Related Art

Respiratory apparatus commonly have the ability to alter the humidity of the breathable gas in order to reduce drying of the patient's airway and consequent patient discomfort and associated complications. The use of a humidifier placed between the flow generator and the patient mask, produces humidified gas that minimizes drying of the nasal mucosa and increases patient airway comfort. In addition in cooler climates, warm air applied generally to the face area in and about the mask, as may occur inadvertently by a leak, is more comfortable than cold air.

Many humidifier types are available, although the most convenient form is one that is either integrated with or configured to be coupled to the relevant respiratory apparatus. While passive humidifiers can provide some relief, generally a heated humidifier is required to provide sufficient humidity and temperature to the air so that patient will be comfortable. Humidifiers typically comprise a water tub having a capacity of several hundred milliliters, a heating element for heating the water in the tub, a control to enable the level of humidification to be varied, a gas inlet to receive gas from the flow generator, and a gas outlet adapted to be connected to a tube that delivers the humidified pressurized gas to the patient's mask.

Typically, the heating element is incorporated in a heater plate which sits under, and is in thermal contact with, the water tub.

The humidified air may cool on its path along the conduit from the humidifier to the patient, leading to the phenomenon of "rain-out", or condensation, forming on the inside of the conduit. To counter this, it is known to additionally heat the gas being supplied to the patient by means of a heated wire circuit inserted into the tube that supplies the humidified gas from the humidifier to the patient's mask. Such a system is illustrated in Mosby's Respiratory Care Equipment ($7^{th}$ edition) at page 97.

Alternatively the heating wire circuit may be located in the wall of the wire heated tube. Such a system is described in U.S. Pat. No. 6,918,389 which describes a number of humidifier arrangements for supplying low relative humidity, high temperature humidified gas to the patient. Some of these arrangements include pre- or post-heating of the gas to reduce the relative humidity.

None of these prior art devices provides an entirely satisfactory solution to the provision of comfortable humidified breathable gas to the patient, nor the ease of construction and hygiene requirements and the energy and patient comfort requirements at startup.

SUMMARY OF THE INVENTION

Examples of the present invention aim to provide an alternative PAP system which overcomes or ameliorates the disadvantages of the prior art, or at least provides a useful choice.

According to one aspect, a heated tube is provided to a respiratory apparatus to deliver the warm and/or humidified air and minimise condensation in the tube.

According to another aspect, a heated tube is provided that allows for measurement and/or control of the delivered air temperature.

According to yet another aspect, a failsafe mechanism may be provided to ensure the delivered air temperature does not exceed a safe temperature limit.

According to a further aspect, it is possible to automatically identify the size of the heated tube, e.g. whether the heated tube attached to the humidifier and/or has a 15 mm or 19 mm bore/internal diameter. Automatic adjustment of system performance with different tube sizes reduces need for clinician/patient adjustment of system settings.

According to a still further aspect, the pneumatic performance of the respiratory apparatus may be compensated, for example in the blower drive circuitry, depending on which heated tube is connected.

According to another aspect, it is possible to detect failures in the heated tube, such as high resistance hot spots in the wires or short circuits between the wires part way down the length of the tube.

According to still another aspect, the heated tube may be electrically and pneumatically connected to the humidifier and/or flow generator in a simple attachment process.

According to a further aspect, a heated tube is provided with an electrical circuit that provide a low profile tube and cuff mouldings.

According to yet another aspect, a tube configuration allows for high volume production. The electronic circuit may use standard components readily available for high production volumes.

According to an even further aspect, a heating plate of the humidifier and the heated tube may be controlled to prevent overheating of the heating plate and the heated tube that may occur due to differences between actual temperatures and temperatures provided by temperature sensors.

In one sample embodiment of the technology, a control system for a heated conduit for use in a respiratory apparatus comprises a power supply to provide power to the heated conduit; an over temperature control circuit to prevent the overheating of the heated conduit; a heating control circuit configured to control heating to obtain a desired temperature; a sensing circuit including a sensing resistor configured to indicate the temperature of a sensor positioned in the heated conduit; and a bias generator circuit configured to provide a first source voltage to the sensing circuit so that the temperature of the heated conduit is continuously monitored.

According to another sample embodiment, a conduit for use in a respiratory apparatus for delivering breathable gas to a patient comprises a tube; a helical rib on an outer surface of the tube; a tube circuit comprising at least three wires supported by the helical rib in contact with the outer surface of the tube and a temperature sensor connected to at least one of the three wires to provide a signal to a power supply and controller of the respiratory apparatus; and a first cuff connected to a first end of the tube and a second cuff connected to a second end of the tube, the first cuff being configured to be connected to a patient interface of the respiratory apparatus and the second cuff being configured to be connected to a flow generator or humidifier of the respiratory apparatus.

In another sample embodiment, a respiratory apparatus for delivering breathable gas to a patient comprises a flow generator to generate a supply of breathable gas to be delivered to the patient; a humidifier to vaporize water and to deliver water vapor to humidify the gas; a first gas flow path leading from the flow generator to the humidifier; a second gas flow path leading from the humidifier to the patient interface, at least the second gas flow path comprises a conduit according to at least the preceding paragraph; and a power supply and controller configured to supply and control power to the conduit through the cuff.

In yet another sample embodiment, a PAP system for delivering breathable gas to a patient comprises a flow generator to generate a supply of breathable gas to be delivered to the patient; a humidifier including a heating plate to vaporize water and deliver water vapor to humidify the supply of breathable gas; a heated tube configured to heat and deliver the humidified supply of breathable gas to the patient; a power supply configured to supply power to the heating plate and the heated tube; and a controller configured to control the power supply to prevent overheating of the heating plate and the heated tube.

In a further sample embodiment, a patient interface for use in a respiratory system comprises an assembly configured to sealingly engage the face of a patient; at least one circuit configured to receive a supply of power and send and receive data, a portion of the at least one circuit being removably attachable to a link from which the data and power is supplied; at least one sensor in communication with the at least one circuit; and at least one controller in communication with the at least one circuit.

In a still further sample embodiment, a method of controlling a heated conduit connected to a respiratory apparatus comprises supplying power to the heated conduit; continuously monitoring a temperature of a sensor positioned in the heated conduit; and controlling the power supply to the heated conduit to obtain a desired temperature.

In still another sample embodiment, a method for delivering breathable gas to a patient comprises generating a supply of breathable gas; vaporizing water using a heating plate; delivering water vapor to humidify the supply of breathable gas; heating and delivering the humidified supply of breathable gas to the patient using a heated tube; and controlling a power supply to the heating plate and heated tube to prevent overheating of the heating plate and the heated tube.

BRIEF DESCRIPTION OF THE DRAWINGS

Sample embodiments will be described with reference to the accompanying drawings, in which.

DETAILED DESCRIPTION

PAP System

Figure 1:
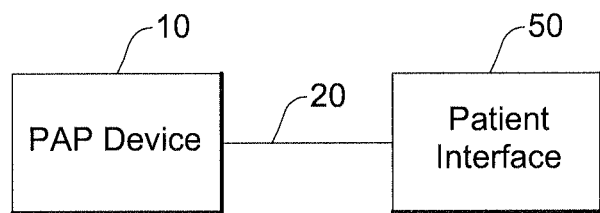
FIG. 1 schematically depicts a PAP system according to a sample embodiment.

As schematically shown in FIG. 1, a Positive Airway Pressure (PAP) system, for example a Continuous Positive Airway Pressure (CPAP) system, generally includes a PAP device 10, an air delivery conduit 20 (also referred to as a tube or tubing), and a patient interface 50. In use, the PAP device 10 generates a supply of pressurized air that is delivered to the patient via an air delivery conduit 20 that includes one end coupled to the outlet of the PAP device 10 and an opposite end coupled to the inlet of the patient interface 50. The patient interface comfortably engages the patient's face and provides a seal. The patient interface or mask may have any suitable configuration as is known in the art, e.g., full-face mask, nasal mask, oro-nasal mask, mouth mask, nasal prongs, etc. Also, headgear may be utilized to comfortably support the patient interface in a desired position on the patient's face.

Figure 2:
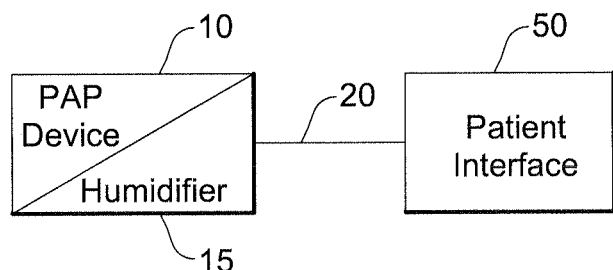
FIG. 2 schematically depicts a PAP system according to another sample embodiment.

In embodiments, a humidifier may be incorporated or integrated into the PAP device or otherwise provided downstream of the PAP device. In such embodiments, the air delivery conduit 20 may be provided between the patient interface 50 and the outlet of the humidifier 15 as schematically shown in FIG. 2.

Figure 3:
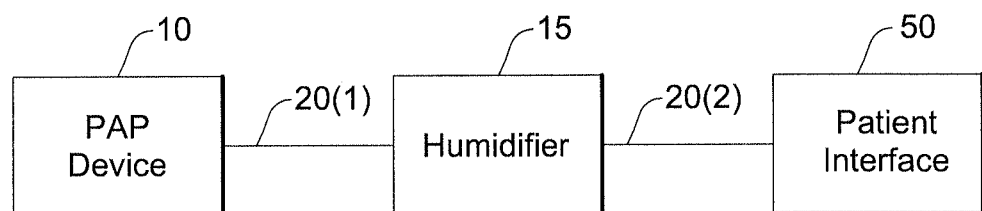
FIG. 3 schematically depicts a PAP system according to another sample embodiment.

It should be appreciated that the air delivery conduit may be provided along the air delivery path in other suitable manners. For example, as schematically shown in FIG. 3, the humidifier 15 may be a separate component from the PAP device 10 so that an air delivery conduit 20(1) is placed between the PAP device 10 and the humidifier 15 and another air delivery conduit 20(2) is placed between the humidifier 15 and the patient interface 50.

Generally, a heated humidifier is used to provide sufficient humidity and temperature to the air so that the patient will be comfortable. In such embodiment, the air delivery conduit may be heated to heat the gas and prevent "rain-out" or condensation forming on the inside of the conduit as the gas is supplied to the patient. In this arrangement, the air delivery conduit may include one or more wires or sensors associated with heating.

As described below, each end of the air delivery conduit includes a cuff structured to attach the tube to the patient interface, PAP device, and/or humidifier. The cuffs differ for non-heated tubes and heated tubes, e.g., cuffs for heated tubes accommodate sensors or electronics/wiring associated with heating.

While the cuff is described as being implemented into a CPAP system of the type described above, it may be implemented into other tubing arrangements for conveying gas or liquid. That is, the CPAP system is merely exemplary, and aspects of the present invention may be incorporated into other suitable arrangements.

Referring to FIGS. 4-7, a PAP system 10 according to a sample embodiment comprises a flow generator, or blower, 12 and a humidifier 15. The flow generator 12 is configured to generate a flow of breathable gas having a pressure of, for example, about 2-30 cm $H_2O$. The flow generator comprises a power button 2 to turn the PAP system on and off. A display 4 is provided to display interactive menus and information regarding the operation of the PAP system to the user or operator. The user or operator may select menus and/or information through inputs 6, which may be, for example, buttons or keys. A push button dial 8 may also allow the user or operator to select information and/or menus. The inputs 6 and the push button dial 8 may be used together to select information and/or menus. For example, one or both of the inputs 6 may be pressed and the dial 8 may be rotated to display desired information or menu on the display 4 and the dial 8 may then be pressed to select particular information to be displayed or a particular mode of operation of the PAP system.

The humidifier 15 comprises a humidifier chamber 16 and a lid 18 which is pivotable between an open and a closed position. A water chamber, or tub, 14 is provided in the humidifier chamber 16 and is covered by the lid 18 when the lid 18 is in the closed position. A seal 19 is provided to the lid 18. The lid 18 includes a window 30 to allow visual inspection of the contents of the humidifier tub 14. The seal 19 includes an aperture 31 that corresponds to the position of the window 30 of the lid 18. In the closed position of the lid 18, the seal 19 contacts the tub 14 to ensure good thermal contact between a bottom of the tub 14 and a heating plate (not shown) provided in the bottom of the humidifier chamber 16 as disclosed, for example, in WO 2010/031126 A1. The tub 14 comprises a base, or bottom, that conducts heat from the heating plate to a supply of water provided in the tub 14. Such tubs are disclosed in WO 2010/031126 A1.

Figure 4:
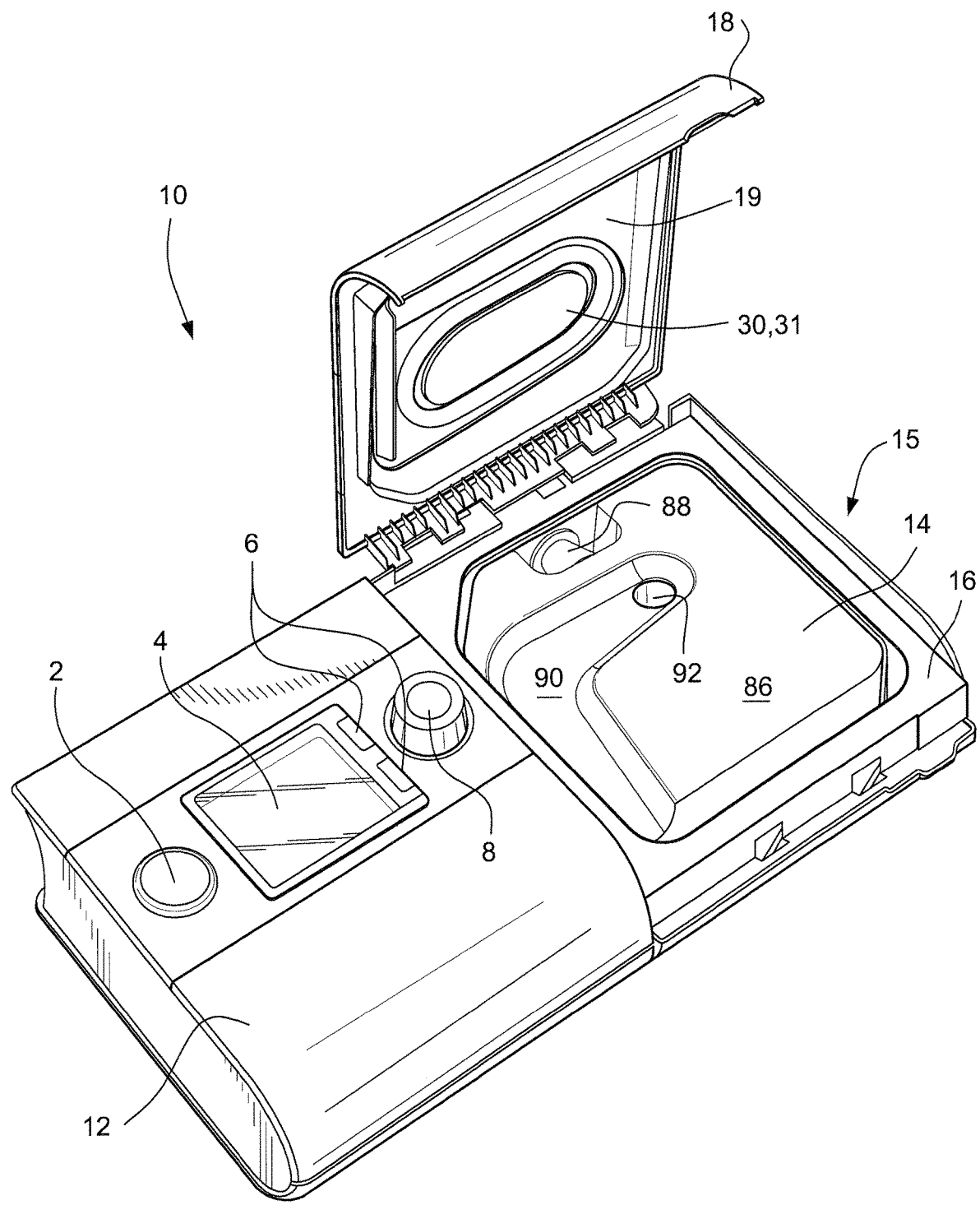
FIG. 4 schematically depicts of a PAP system including a flow generator and humidifier according to a sample embodiment.
Figure 5:
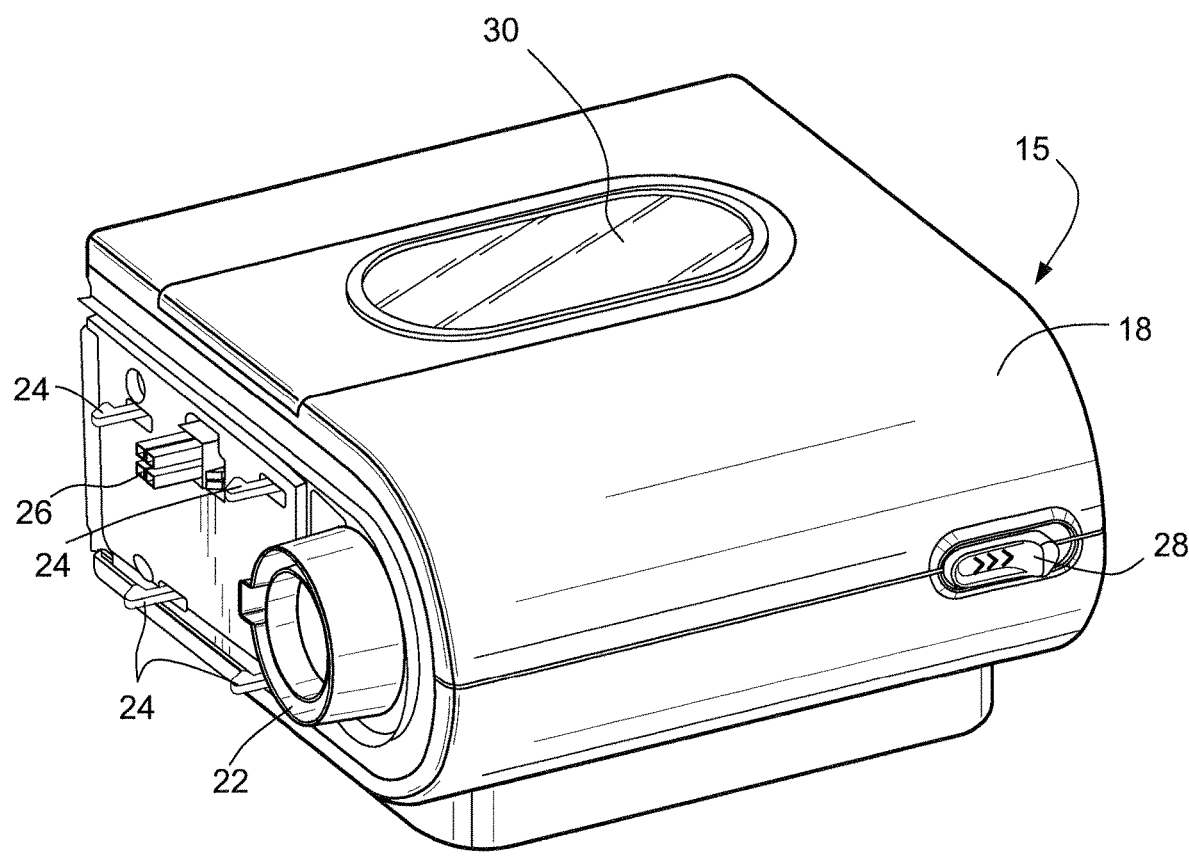
FIGS. 5 through 7 schematically depict the humidifier of FIG. 4.

As shown in FIGS. 4 and 5, the humidifier 15 is connectable to the flow generator 12 by connectors, or latches, 24. The latches 24 may be, for example, spring biased latches that engage corresponding recesses (not shown) in the flow generator 12. An electrical connector 26 is provided to electrically connect the flow generator 12 to the humidifier 14. Electrical power may be provided from the flow generator 12 to the humidifier 14, although it should be appreciated that the humidifier may be provided with its own power source. Control signals may also be provided from the flow generator 12 to the humidifier 14 through the electrical connector 26.

As shown in FIG. 4, the tub 14 comprises a tub lid 86 that is configured to direct a flow of breathable gas generated by the flow generator 12 along a channel 90 in the tub lid 86 and through an outlet 92 of the channel 90 into the tub 14. The humidifier chamber 16 includes an air inlet 22 configured to receive the flow of breathable gas generated by the flow generator 12 when the humidifier 15 is connected to the flow generator 12 by the latches 24. The inlet 22 directs the flow into the channel 90 in the tub top 86 of the water tub 20. The flow is directed by the channel 90 to the outlet 92 into the water tub 14. The tub 14 includes an outlet 88 for the humidified flow of breathable gas. A tube connector 70 (FIG. 7) is provided at a rear portion of the humidifier 15 in communication with the outlet 88. In addition, a ring 76 is provided to the outlet tube 70. It should be appreciated that the tube connector 70 may be provided on a side, or the front, of the humidifier 15. The tube connector 70 is configured for connection to a hose, tube, or conduit to a tube that is configured to deliver the humidified flow to patient interface, e.g. a mask, as described in more detail herein.

It should be appreciated that the humidifier 15 may include its own control system, or controller, for example, a microprocessor provided on a printed circuit board (PCB). The PCB may be located in the wall of the humidifier chamber 16 and may include a light, e.g. an LED, to illuminate the contents of the tub 14 to permit visual inspection of the water level. It should also be appreciated that the flow generator 12 comprises a control system, or controller, that communicates with the controller of the humidifier 15 when the flow generator 12 and the humidifier 15 are electrically connected. It should be further appreciated that the flow generator and/or the humidifier may include a plurality of sensors, including for example, an ambient humidity sensor that may be configured to detect, for example, absolute ambient humidity and which may include an absolute humidity sensor or a temperature sensor to detect an ambient temperature and a relative humidity sensor to detect an relative humidity from which the ambient absolute humidity may be calculated. The plurality of sensors may also include, for example, an ambient pressure sensor to detect an ambient pressure, a flow sensor to detect a flow of breathable gas generated by the flow generator, and/or a temperature sensor to detect a temperature of a supply of water contained in the tub 14 of the humidifier 15 or the temperature of the heating plate of the humidifier 15. Such an arrangement is shown, for example, in U.S. Patent Application Publication 2009/0223514 A1. The PAP system 10 may be operated according to various control algorithms stored in the controller(s) of the flow generator 12 and/or the humidifier 15. Such control algorithms are disclosed in, for example, U.S. Patent Application Publication 2009/02223514 A1.

Figure 6:
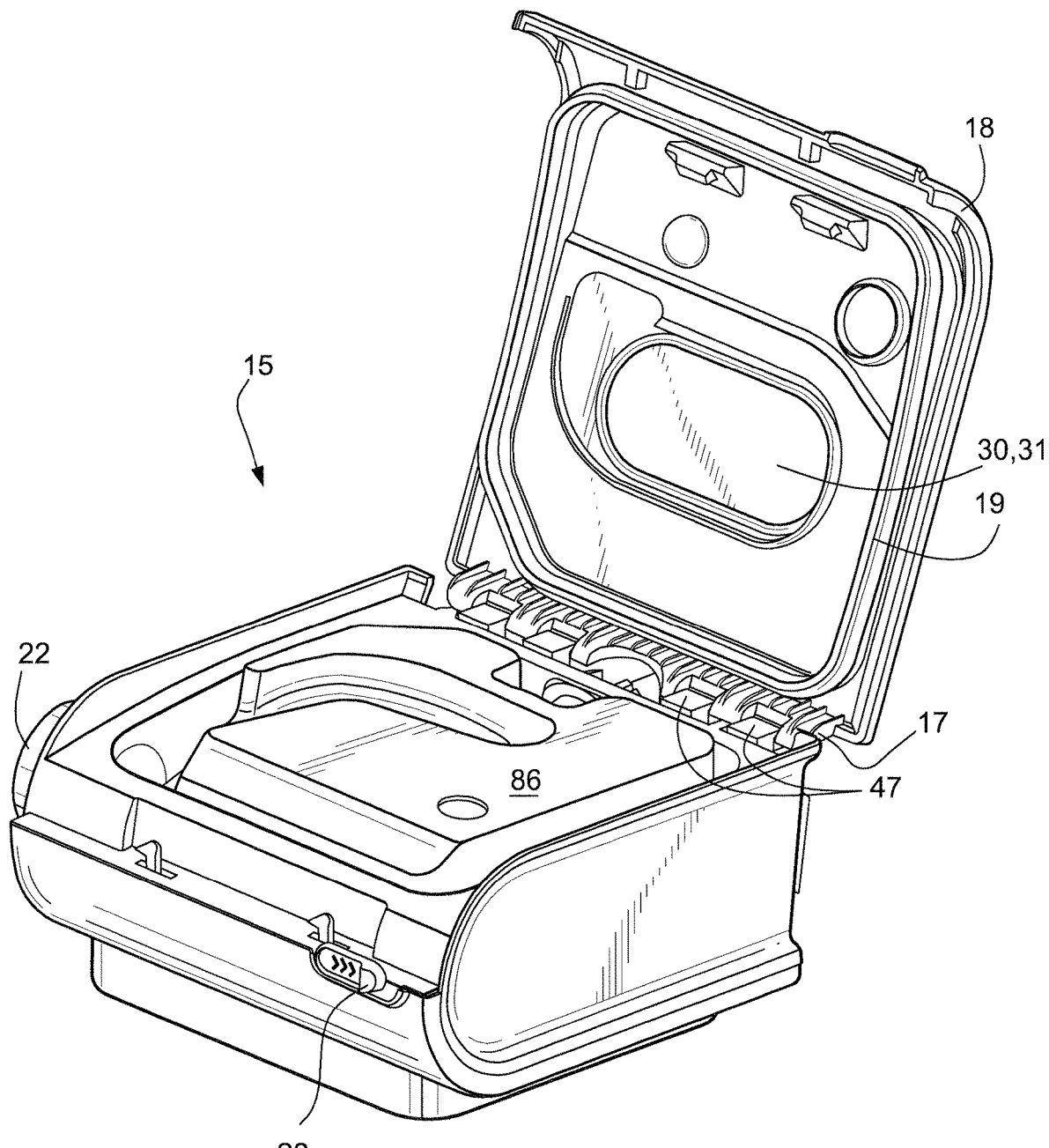

The humidifier 15 comprises the humidifier chamber 16 and the lid 18 which is pivotally connected to the humidifier chamber 16. As shown in FIG. 6, the lid 18 comprises a hinge portion 17 that is hinged to hinge portions 47 provided on the humidifier chamber 16. An opening member 28 is provided for releasing the lid 18 to allow the lid to be pivoted to the open position shown in FIGS. 4 and 6 as described in WO 2010/031126 A1.

Figure 7:
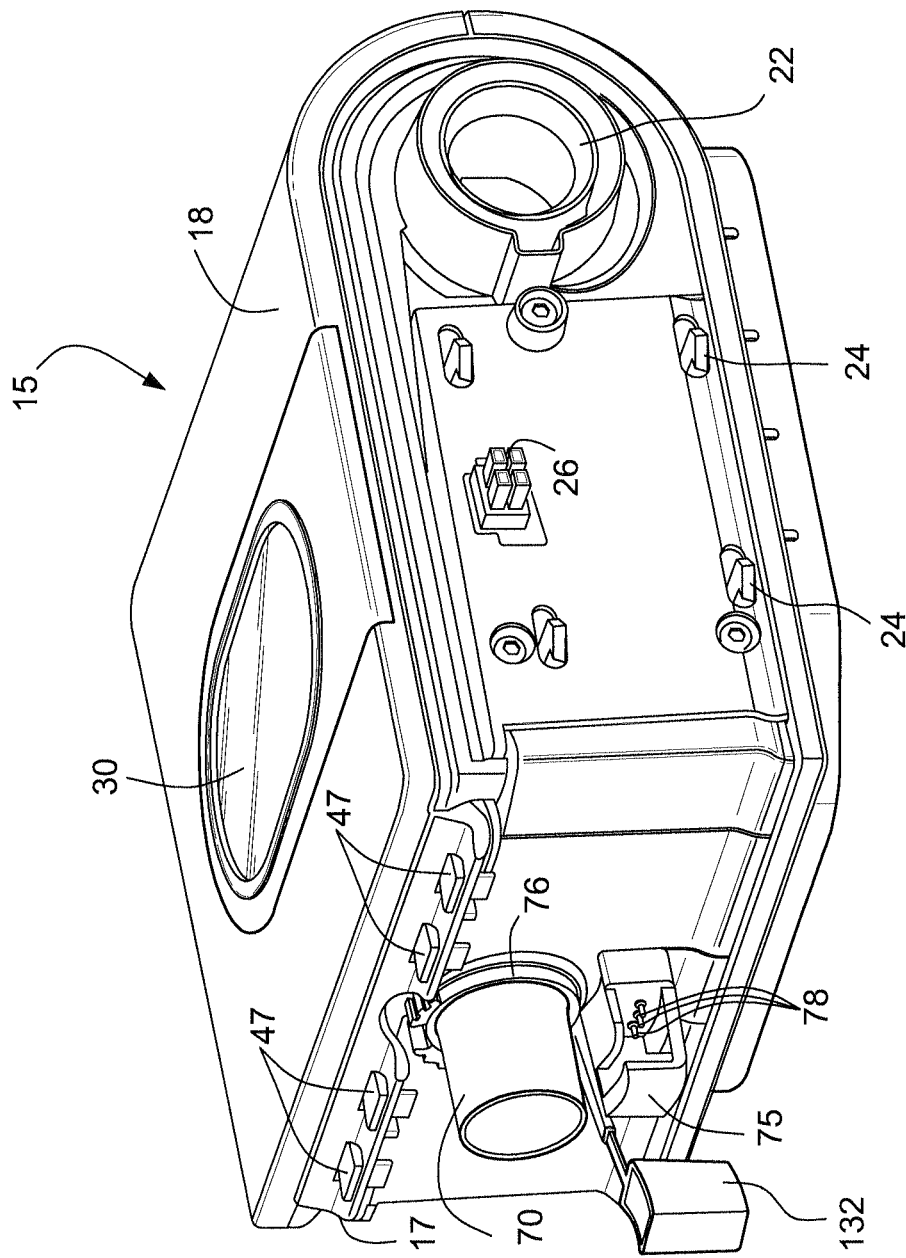

Referring to FIG. 7, the humidifier comprises the tube connector 70 and a tube electrical connector 75. The tube connector 70 and the tube electrical connector 75 provide the ability to connect both a standard tube and a heated tube. As shown in FIG. 7, the tube electrical connector 75 comprises a plurality of contacts 78. The tube electrical connector 75 and the contacts 78 are provided separately from the tube connector 70. A heated tube having corresponding electrical connections, e.g. terminals, may be provided in a rotational snap fit with the tube electrical connector 75 as described in more detail below. This type of connection provides ease of connection and reduces the tolerance stack of the respiratory apparatus 10. A cover 132 may be connected to the back wall of the humidifier 15 to cover the tube connector 75 and the contacts 78 when a non-heated tube is connected to the tube connector 70. The cover 132 may be formed of a pliable rubber or other suitable flexible material. Alternatively the cover 132 may be a separate component, not attached to the humidifier that may be inserted over the tube electrical connector 75.

Heated Tube/Conduit

Figure 8:
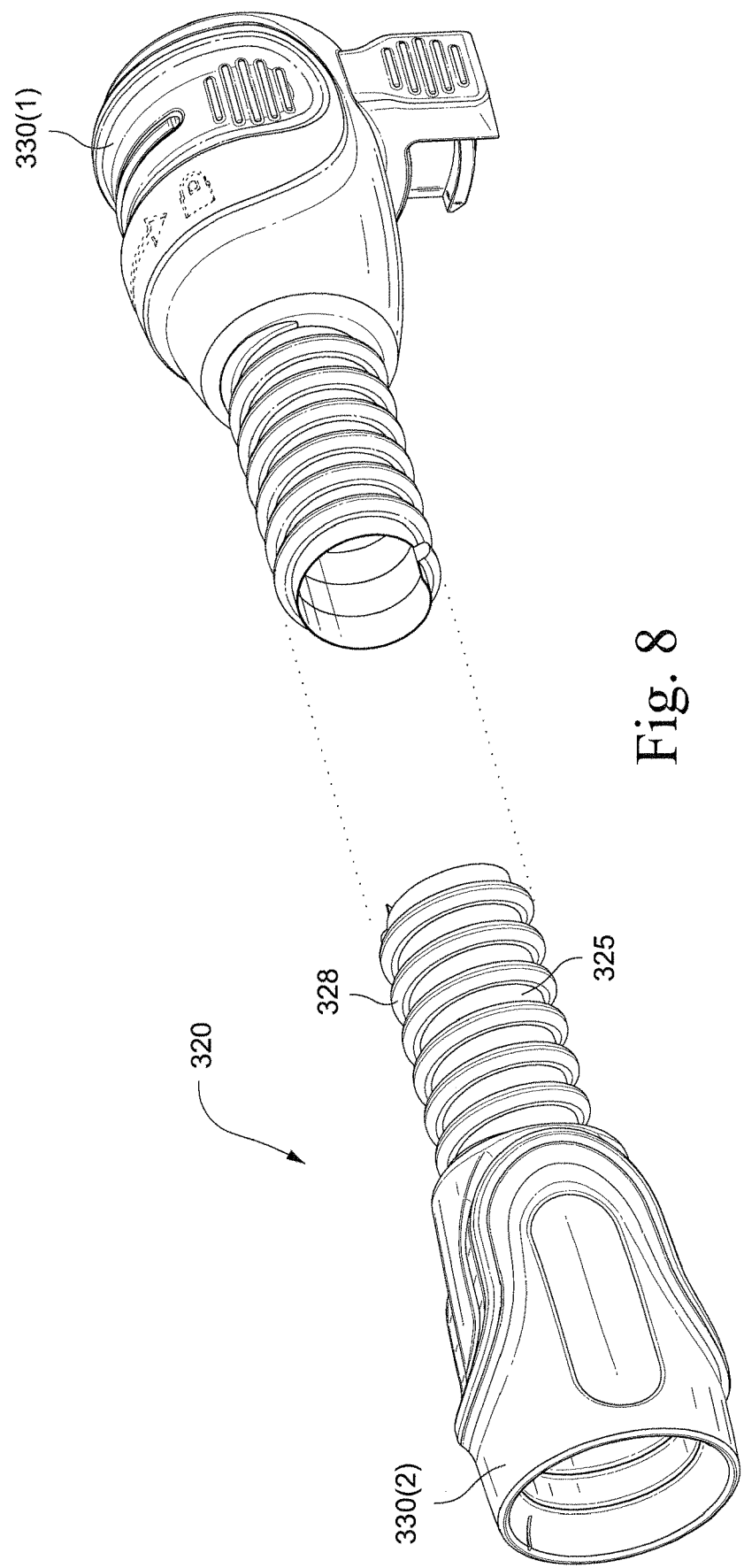
FIG. 8 schematically depicts a heated tube according to a sample embodiment.
Figure 9:
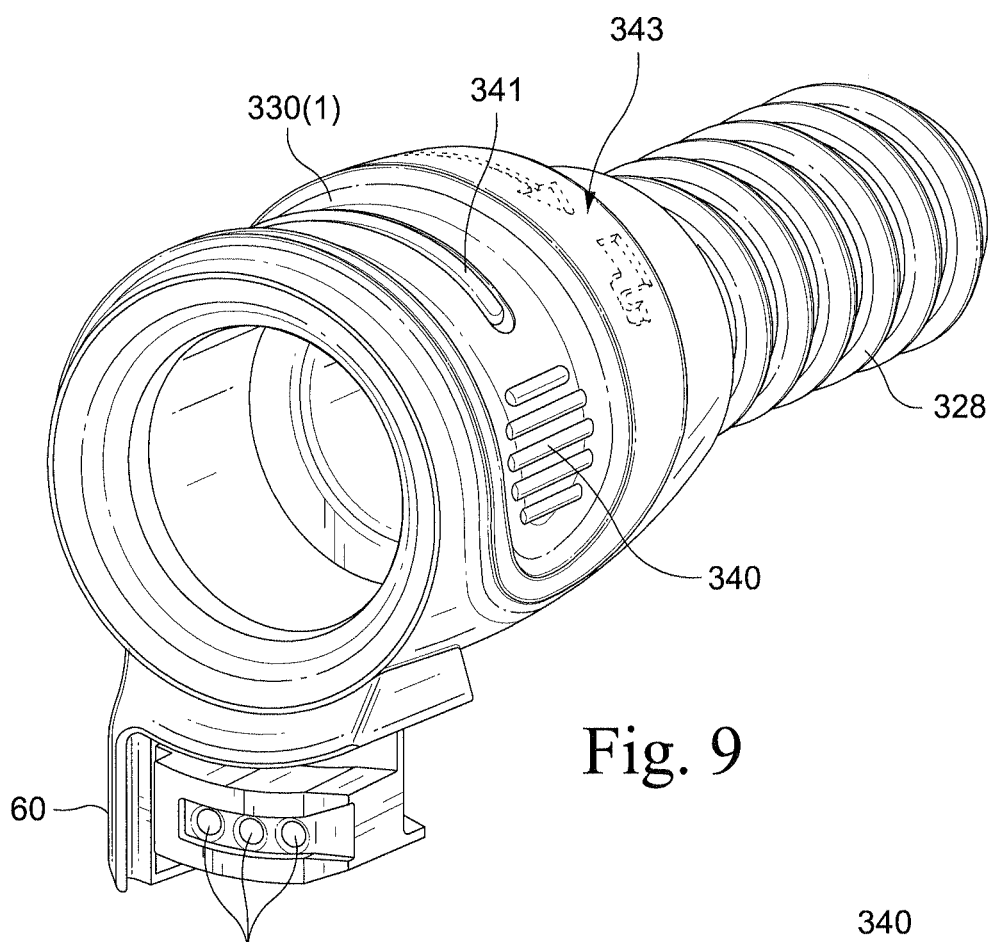
FIGS. 9 through 13 schematically depict a connector, or cuff, of the tube of FIG. 8 at an end of the tube configured to be connected to a humidifier.
Figure 10:
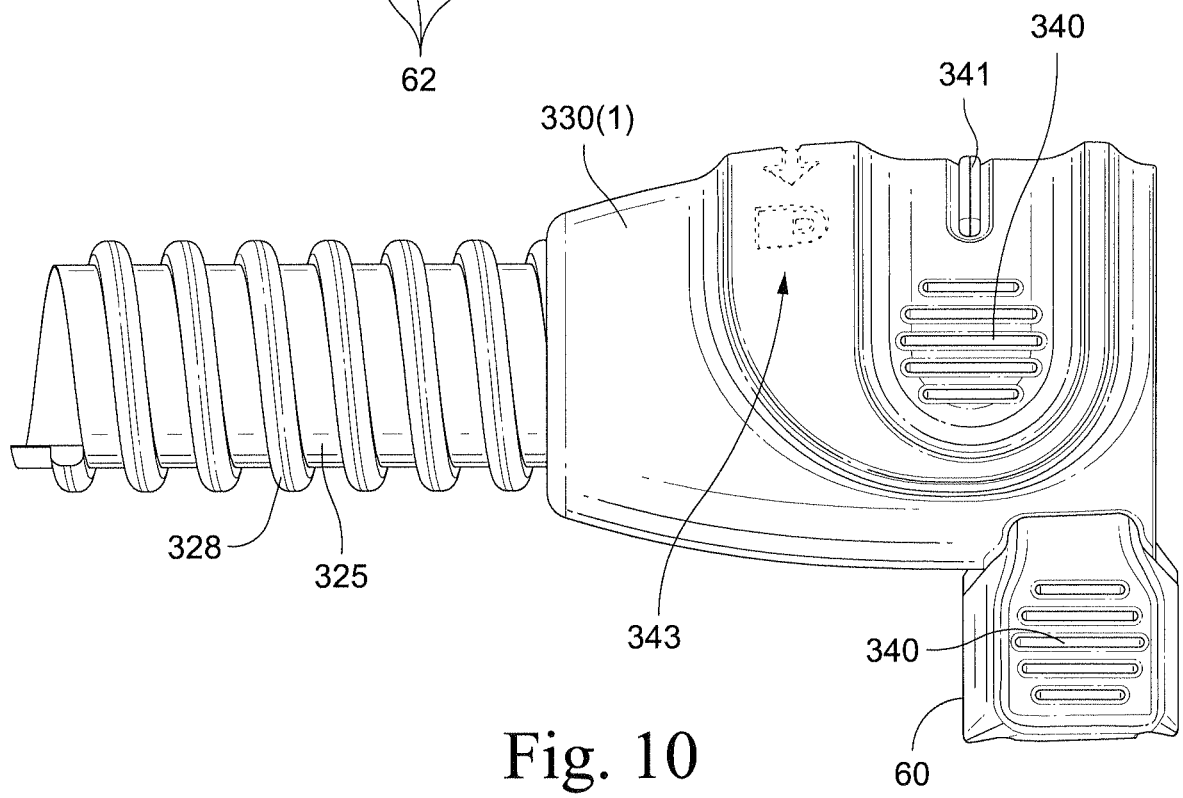
Figure 11:
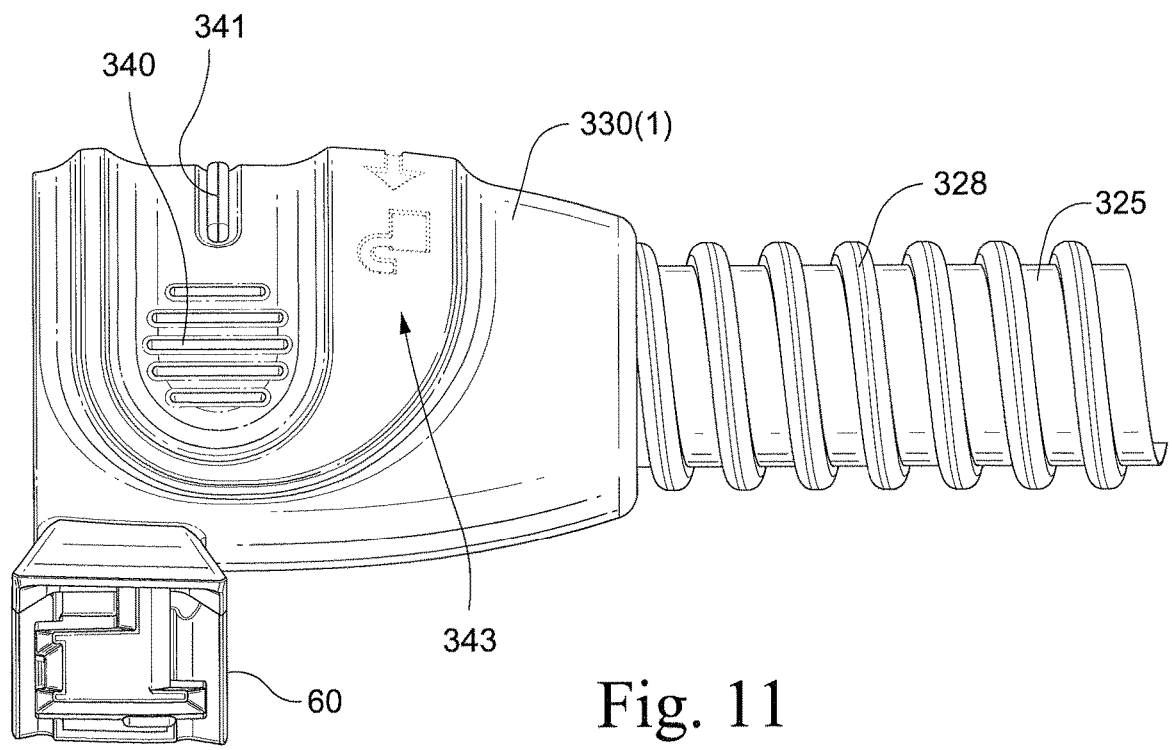
Figure 12:
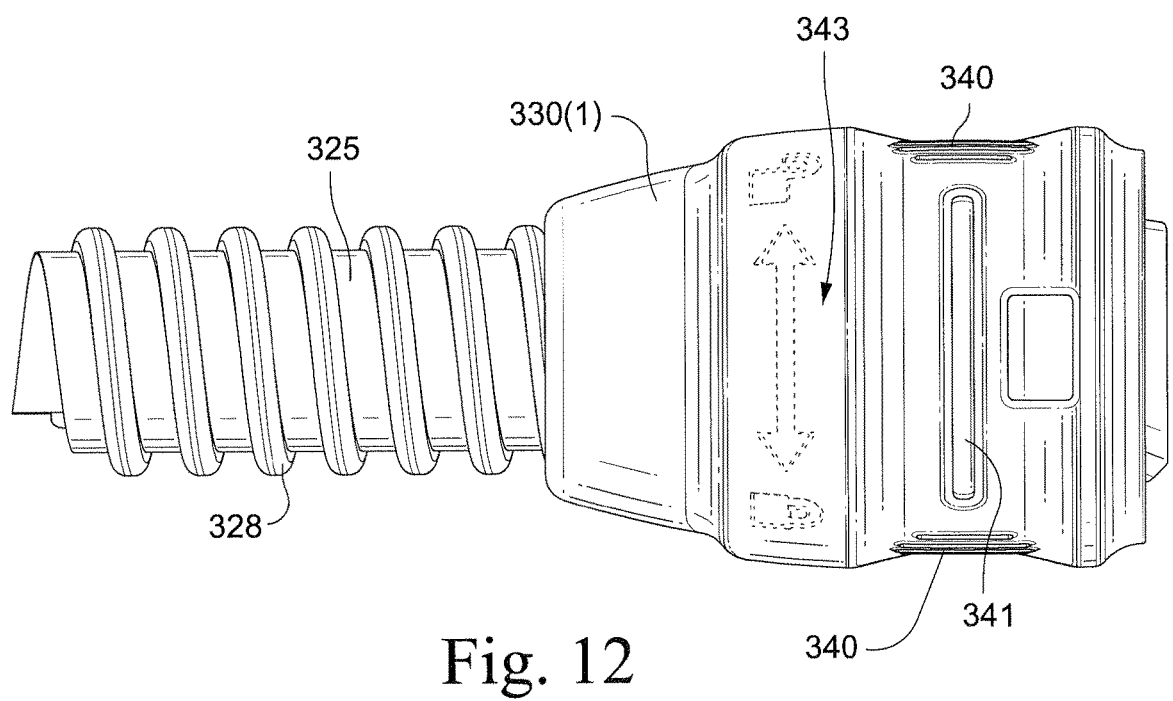
Figure 15:
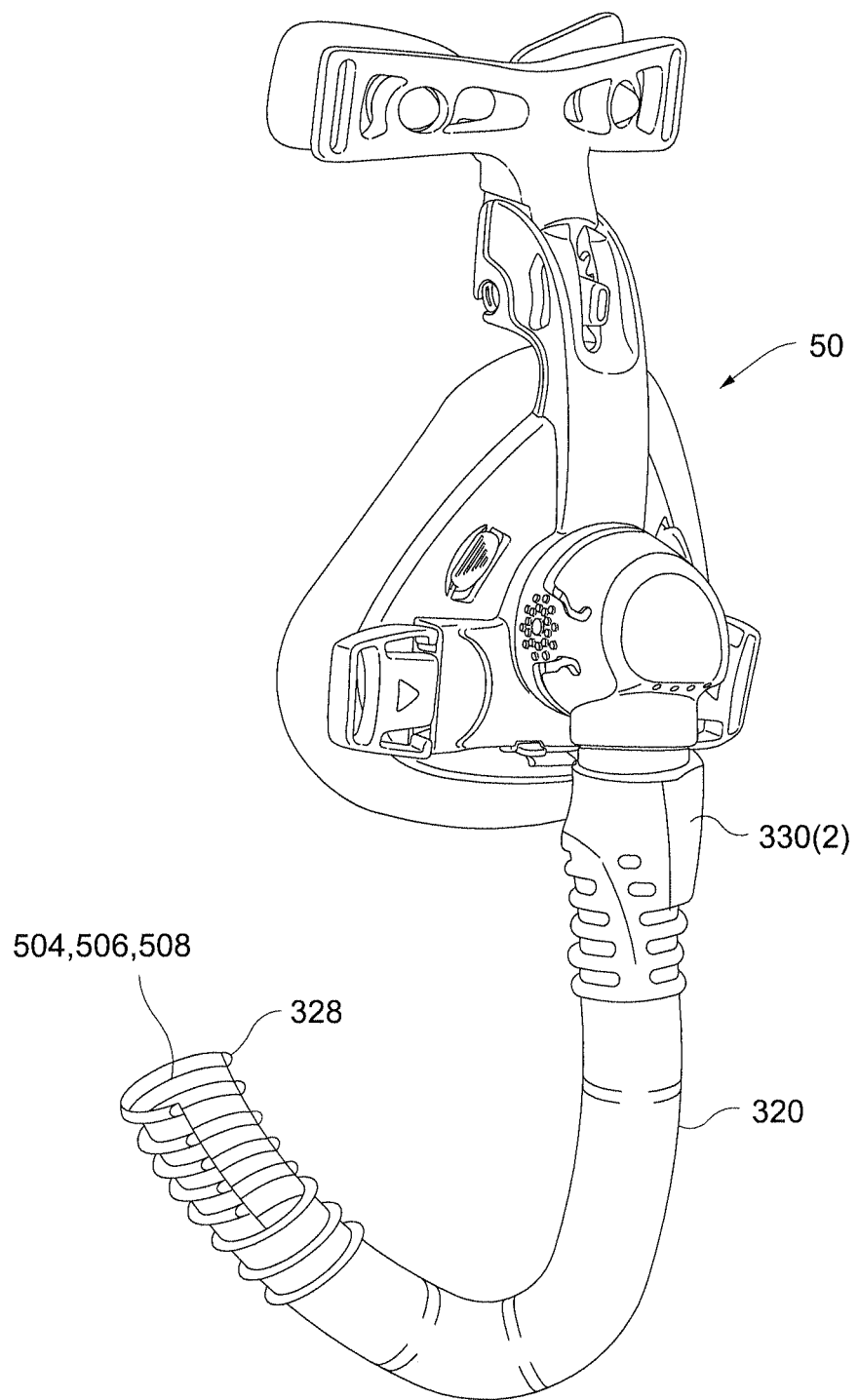
FIG. 15 schematically depicts an end of the tube of FIG. 8 connected to a patient interface.
Figure 16:
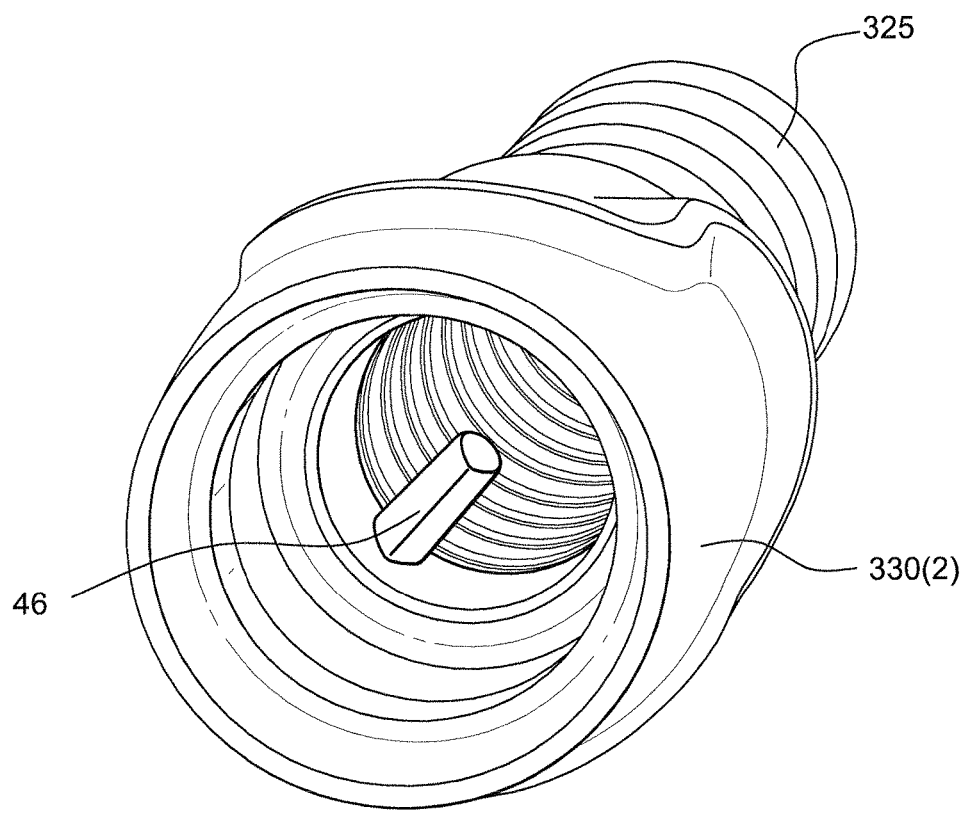
FIGS. 16 and 17 schematically depict a connector, or cuff, of the end of the tube of FIG. 8 configured to be connected to a patient interface.
Figure 17:
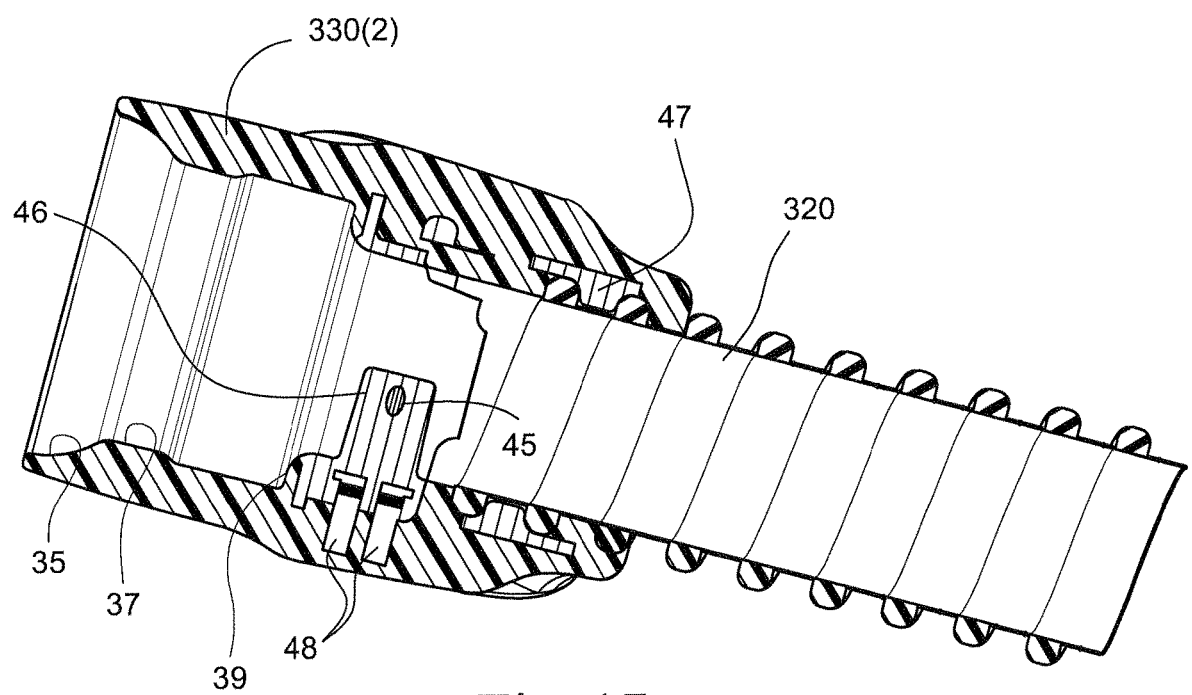

FIG. 8 illustrates an embodiment of a heated air delivery conduit or tube. The heated tube 320 comprises a flexible tube 325, a first connector, or cuff, 330(1) provided to one end of the tube 325 and configured and arranged to engage the tube connector 70 and the tube electrical connector of the humidifier 15, and a second cuff 330(2) provided to the opposite end of the tube 325 and configured and arranged to engage the inlet (e.g. a swivel elbow) of a patient interface 50, as shown in FIG. 15. The heated tube 320 may be, for example, as disclosed in U.S. Patent Application Publication 2010/0116272 A1.

Figure 18:
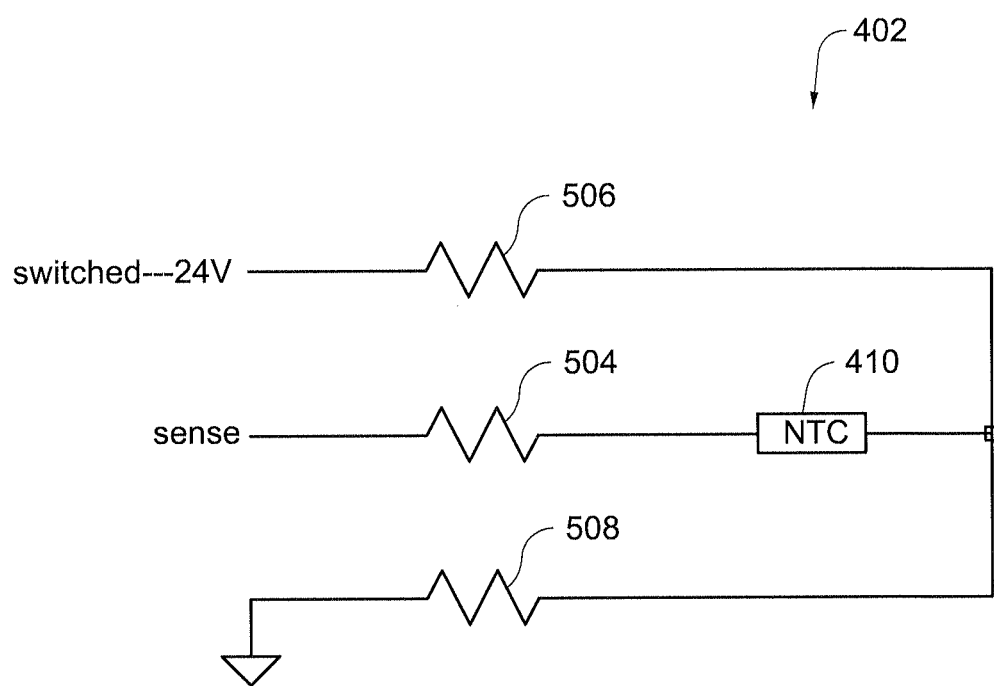
FIG. 18 schematically depicts a wiring configuration for the heated tube of FIG. 8.

The tube 320 is structured to conduct heat along at least a portion of its length. For example, spiral ribbing 328 of the tube 325 may be structured to support three wires 504, 506, 508 (FIGS. 15 and 18). In addition, the heated tube 320 may be structured to support one or more sensing apparatus, e.g. a flow sensor and/or a temperature sensor, etc. Further details of such tubing are disclosed in U.S. Patent Application Publication 2008/0105257 A1.

In the illustrated embodiment, the cuffs 330(1), 330(2) are different from one another as described below. However, each cuff provides structure for attaching, sealing, and retaining the cuff to a respective connector, e.g., 22 mm ISO-taper connector.

Figure 13:
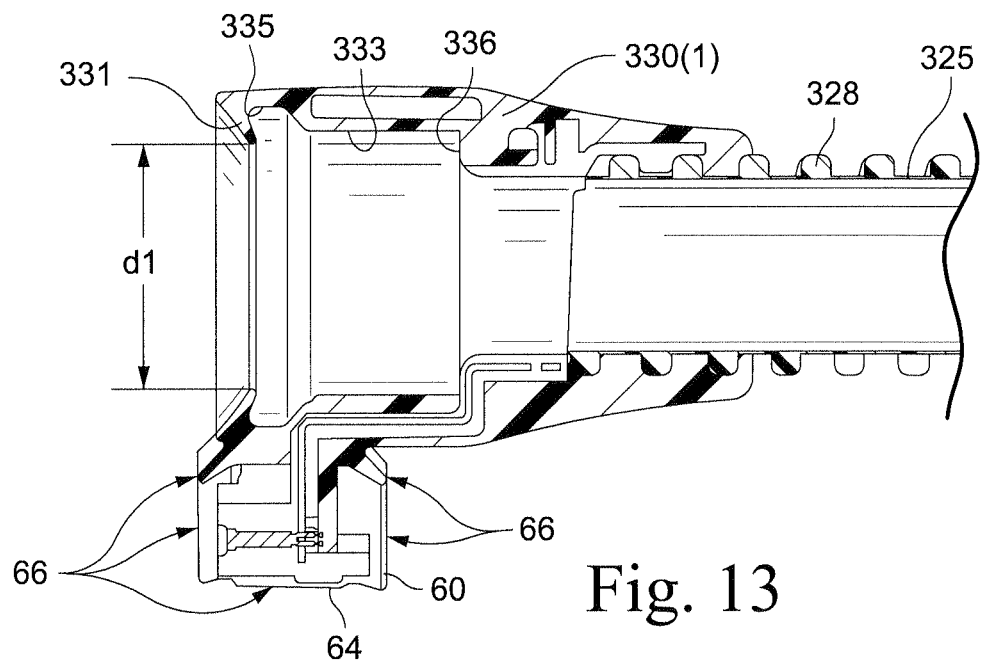
Figure 14:
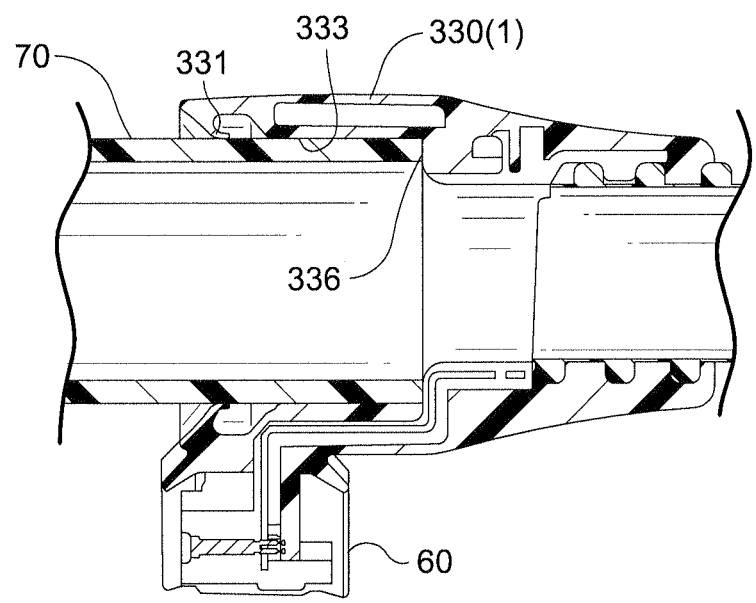
FIG. 14 schematically depicts the end of the tube of FIGS. 9 through 13 connected to the humidifier of FIGS. 5 through 7.

The opening of the cuff 330(1) includes a radial lip seal or sealing lip 331 along the interior surface thereof. As shown in FIG. 13, the radial lip seal 331, in its relaxed, undeformed shape, provides an internal diameter d1 that is smaller than the external diameter of the tube connector 70. For example, the internal diameter may be less than about 22 mm (e.g., about 19-21 mm or less) for use with a standard 22 mm connector. In use, as best shown in FIG. 14, the sealing lip 331 is structured to resiliently deform upon engagement with the tube connector 70 so as to provide a gas tight seal against the exterior surface of the tube connector 70. For example, the sealing lip 331 provides a flexible protrusion structured to resiliently deflect from a first position (FIG. 13) and into a second position (FIG. 14) within a cut-out 335.

As illustrated, the sealing lip 331 tapers outwardly towards the cuff opening to provide a sufficient lead in for aligning and engaging the cuff 330(1) with the tube connector 70.

The interior surface 333 axially inwardly from the sealing lip 331 provides an internal diameter that is substantially the same as the external diameter of the tube connector 70, e.g., about 22 mm for use with a standard 22 mm connector. A stop surface or flanged faced 336 within the cuff 330(1) provides a stop to prevent the tube connector 70 from inserting further into the cuff 330(1).

FIGS. 9-14 illustrate the cuff 330(1) structured for attachment to the humidifier 15. The cuff 330(1) includes an electrical connector 60 that is configured to provide an electrical connection with the humidifier 15 for operating the heating wires 504, 506, 508 (FIG. 15) provided to the tube 320. The electrical connector 60 includes terminals 62 that are configured to receive the contacts 78 of the tube electrical connector 75 of the humidifier 15 when the cuff 330(1) is connected to the tube connector 70 of the humidifier 15. The electrical connector 60 provides a retention function for the cuff 330(1). Retention is via a rotate-and-lock system to align the terminals 62 of the electrical connector 60 with the contacts 78 of the tube electrical connector 75 of the humidifier 15. The electrical connector 60 provides a heel 64 structured to be rotated into engagement with the tube electrical connector 75 such that the heel 64 locks into a cam or recess provided to the tube electrical connector 75 of the humidifier 15. When engaged, the heel 64 axially locks the cuff 330(1) into place. To release, the cuff 330(1) is rotated out of engagement with the tube electrical connector 75 to disengage the heel 64. As shown in FIG. 13, a seal 66 extends from the front, back, side, and bottom of the electrical connector 60 and seals against the tube electrical connector 75 of the humidifier 15 to prevent water spillage onto the electrical contacts 78 and the terminals 62.

The cuff 330(1) may comprise finger grips 340 along opposing sides thereof and along an edge of the electrical connector 60. The cuff 330(1) may also comprise an identifying strip 341 (e.g., orange strip) to identify the tube as a heated tube. A similar identifying strip may be provided to the user interface of the PAP system 10 and configured to illuminate or otherwise signal when the heated tube is operative, e.g., heating up, heated, etc. In addition, indicia and/or images 343 may be provided to the cuff 330(1) to indicate directions for locking and unlocking the cuff 330(1) with respect to the humidifier 15.

Referring to FIGS. 15-18, the cuff 330(2) at the opposite end of the heated tube 320 is configured for attachment to the patient interface (e.g. mask) 50. The cuff 330(2) comprises a sensor 45 located (e.g., molded into) within the rear portion of the cuff. The cuff 330(2) includes a curved entry surface 35, a sealing and retention bead 37, and a stop surface 39 to aid connection of the heated tube 320 to the patient interface 50.

The sensor 45 is provided to a fixture 46 within the cuff. In the illustrated embodiment, the fixture 46 is wing-shaped (e.g. air-foil shaped) to optimize convective heat transfer over a range of flow rates, while minimizing noise or pressure drop. However, the fixture 46 may have other suitable shapes and/or textures. The cuff 330(2) may be formed by, for example, overmolding on a pre-block 47, or any method disclosed, for example, in U.S. Patent Application Publication 2008/0105257 A1, which is incorporated herein by reference in its entirety. The sensor 45 may be connected to the wires 504, 506, 508 in the heated tube 320 by a lead frame 48. The temperature sensed by the sensor 45 may be provided as a signal from the middle wire 504 through the lead frame 48 to a controller located in the humidifier 15 and/or the PAP system 10.

As shown in FIG. 18, the sensor 45 may take the form of a thermistor 410 formed of a Negative Temperature Coefficient (NTC) material. As described in more detail below, the middle wire 504 of the three wires 504, 506, 508 of the tube circuit 402 may be connected to the thermistor 410 and provide the temperature sensing signal to the controller. Two wires 506, 508 may be joined together at the lead frame 48 to complete the heating circuit. The third wire 504 provides a connection to the NTC thermistor which may be attached to the mid-point of the heating circuit. The two heating wires 506, 508 may be low ohmic value resistors to apply heat to the tube wall and therefore to the air being delivered to the patient. The signal wire 504 may be fitted with the thermistor 410 located at the patient interface end of the heated tube 320. The signal wire 504 monitors the temperature of the air at the patient interface end of the heated tube and detects any imbalance between the bridge formed by the two heater wires 506, 508. The imbalance may be used to detect a fault condition, for example high impedance or an open circuit and low impedance or a short circuit.

Heated Tube Control

Figure 19:
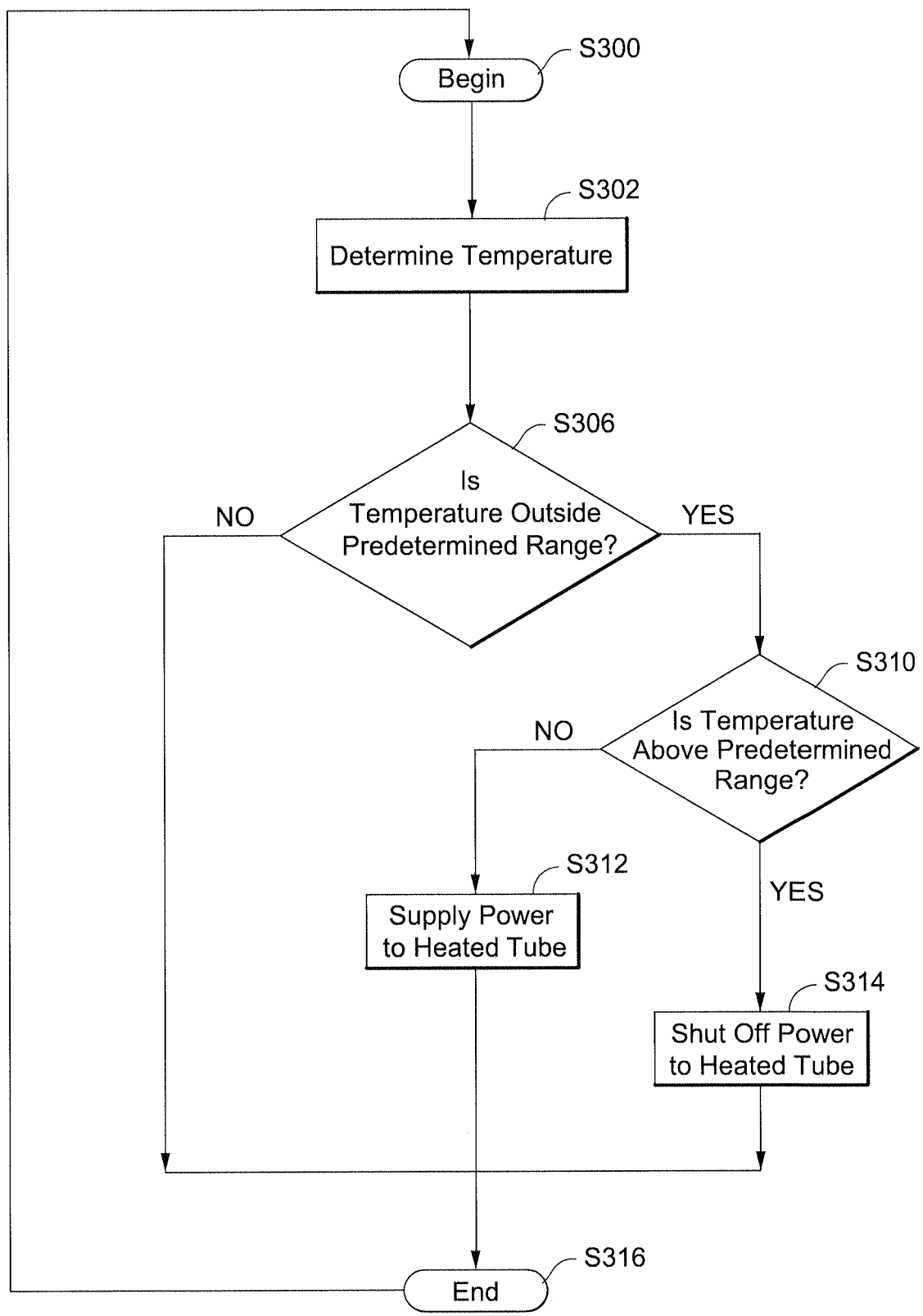
FIG. 19 schematically depicts a sample embodiment of an algorithm for controlling the heated tube.

The heated tube 320 may be used to deliver the comfort of warm, humidified air and minimise condensation in the tubing. Referring to FIG. 19, an algorithm for controlling a heated tube is shown. The algorithm starts at S300 and determines the temperature sensed by a temperature sensor in the heated tube (e.g. thermistor 410) in S302. The algorithm proceeds to S306 and determines if the sensed temperature is outside a predetermined range. If the temperature of the heated tube is not outside the predetermined range (S306: No), the algorithm ends in S316. Conversely, if the temperature is outside the predetermined range (S306: Yes) the algorithm proceeds to S310 and it is determined if the temperature is above the predetermined range. If the temperature is below the predetermined range (S310: No), the algorithm proceeds to S312 and power is supplied to the heated tube. If the sensed temperature is above the predetermined range (S310: Yes), the algorithm proceeds to S314 shuts off power to the heated tube. After the completion of S312 or S314 the algorithm returns to the beginning in S300, thus providing temperature control for the heated tube.

The control of the heated tube may involve several considerations. One consideration is to measure and control the delivered air temperature in the heated tube system with a low cost tube assembly. Another consideration is, for safety, a failsafe mechanism may be provided to ensure the delivered air temperature does not exceed a safe temperature limit. Still another consideration is that it may be desirable to automatically identify whether the heated tube that is attached to the humidifier and/or flow generator has a 15 mm or 19 mm internal diameter. The pneumatic performance of the system may require compensation in the blower drive circuitry depending on which internal diameter tube is present.

According to another consideration, for safety, it is desirable to detect failures in the heated tube, such as high resistance hot spots in the wires or short circuits between the wires part way down the length of the tubing. A further consideration is that the heated tube may make both electrical and pneumatic connection to the humidifier in a simple attachment process.

Current heated tube systems do not directly regulate the temperature of the air delivered. They are implemented as open loop control of tube heating using a fixed power level. Although it may be possible to implement a thermal cut-out switch within the structure of the tube, these devices are relatively large and require additional circuit connections and mechanical mounting that add significant complexity to the tube.

Heated Tube Control—Temperature Sensing with Active Over Temperature Protection

Figure 20:
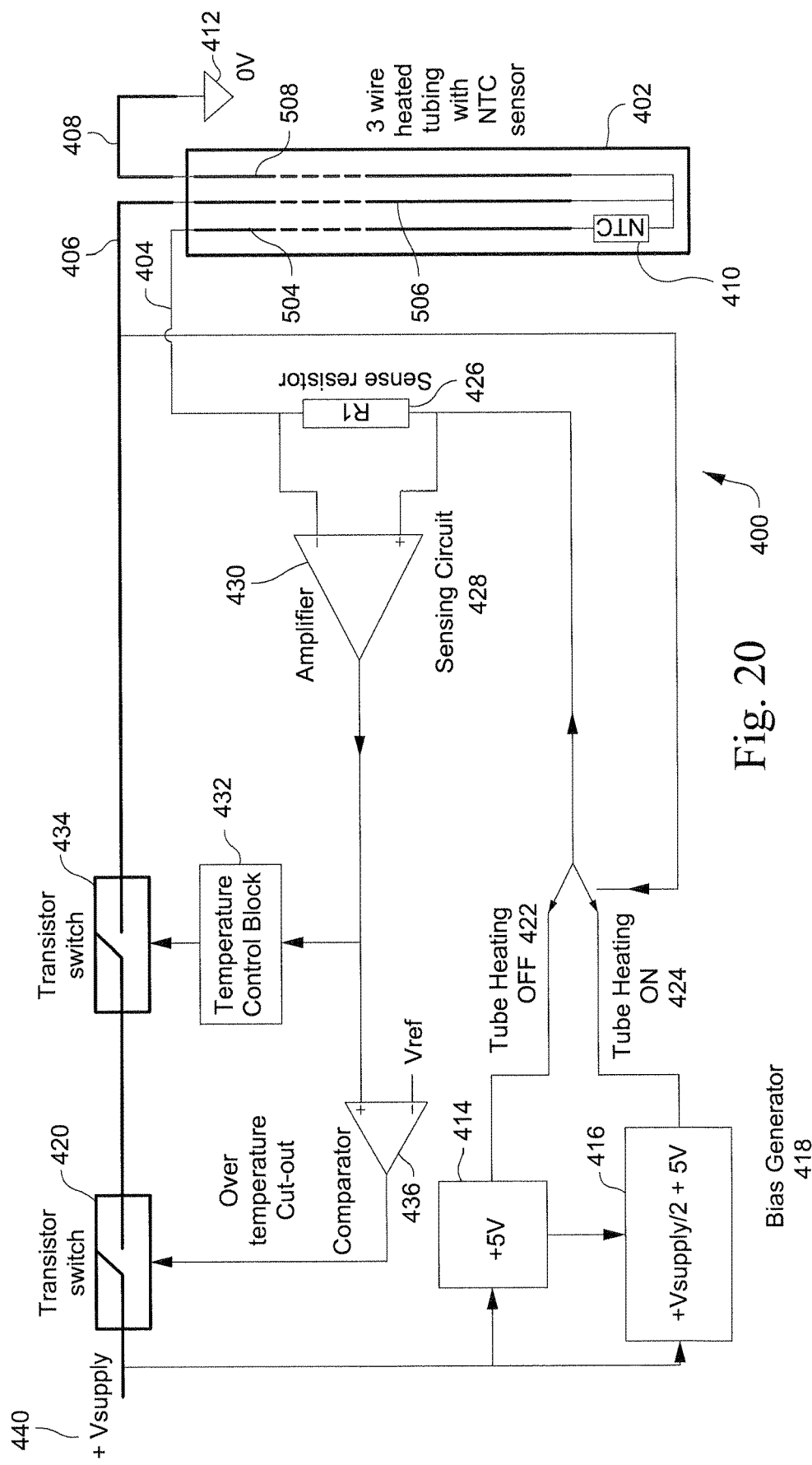
FIG. 20 schematically depicts a circuit according to another sample embodiment that senses a temperature at the patient interface and provides active over temperature protection.

Referring to FIG. 20, a circuit configuration 400 according to a sample embodiment allows control of the tube air temperature using a sensor at the output (mask) end of the tube. The heated tube circuit 402 comprises the three wires 504,506, 508 and the temperature sensor, e.g. the NTC thermistor 410. The heater wires 404, 406, 408 are used in the sensing and control circuit to create a lower cost heating and sensing system with only three wires. As shown in FIG. 18, the three wires 504, 506, 508 of the heated tube circuit 402 are connected to different components of the sensing and control circuit to provide a sensing wire 404, a power supply wire 406 and a ground wire 408. The sensing and control circuit may be provided in a power supply and controller of the humidifier and/or flow generator. Such a power supply and controller is disclosed in, for example, U.S. Patent Application Publication 2008/0105257 A1.

Referring again to FIG. 20, the circuit configuration 400 comprises a power supply 440, such as a 24V supply voltage, an over-temperature control circuit and a heating control circuit. The over-temperature control circuit comprises a first transistor switch 420 that is turned on when the temperature of the heated tube is below a predetermined temperature and turned off when the temperature is at or above the predetermined temperature. The predetermined temperature is set at a temperature to meet appropriate safety requirements of the heated tube, such as between 30° C. and 45° C., preferably 38° C. to 43° C. Comparator 436 controls the switching of the transistor switch 420. A reference voltage representing the predetermined temperature is compared to the voltage determined from an amplifier 430 from the sensing circuit to ensure the heated tube is not above or equal to the predetermined temperature.

Within the over-temperature control circuit is the heating control circuit which is designed to control the heating of the heated tube to obtain a desired temperature. The desired temperature may be set by the user or determined by the system. The heating control circuit switches the power supply 440 through the heated tube circuit 402 to a ground reference 412. Thus, the temperature sensor 410 moves between ground having 0V and half the supply voltage, e.g. 12V. Heating is supplied to the heated tube circuit 402 from power supply 440 through a second transistor switch 434. Transistor switch 434 is open and closed to turn heating on and off to the heated tube circuit 402 respectively. In one embodiment this transistor switch 434 is switched on and off very rapidly with changes in the duty cycle to control the heating of the tube. However, the switch 434 may be switched on to provide constant heating until a set temperature is reached and then turned off. The temperature of the heated tube is sensed by the temperature sensor 410 and is transmitted through sense wire 404 to sense resistor 426 and sensing circuit 428 comprising amplifier 430. A bias generator circuit 418 provides the source voltage Vcc for the sensing circuit 428 so that the temperature of the heated tube is determined whether the tube is being heated or not. The bias generator circuit 418 generates a reference voltage that is either the Vcc source voltage 414, shown as 5V in this embodiment although other voltages may be used, when the tube heating is off via switch 422 or provides half the voltage supply plus the Vcc source voltage 416, i.e. 5V, when the tube heating is on via switch 424. Thus a constant voltage of Vcc source voltage is provided across the sensing circuit 428 irrespective of the state of the heated tube. The switching of the bias switches 422, 424 is controlled by the transistor switch 434 of the heating control circuit, such that when the transistor switch 434 is closed the tube heating ON switch 424 is active and when the transistor switch 434 is open the tube heating ON switch 424 is inactive. Thus, it is the voltage that is supplied to the heated tube circuit 402 that provides the bias switch.

The sensed temperature signal from the temperature sensor 410 is provided to amplifier 430 that produces a voltage that represents the heated tube temperature. The temperature control block 432 controls the opening and closing of switch 434 to modulate the power delivered to the heated tube circuit to maintain the desired temperature.

The temperature sensor 410 is held at a different circuit potential when the heater is active and when it is inactive. However, the sensor 410 should be continuously monitored to provide a failsafe against over temperature. A bias circuit 418 may be provided for continuous sensing. A bias generator circuit may provide the source voltage for the sensing circuit, a divider network comprising a resistor R1 and the NTC thermistor. This allows continuous temperature monitoring during both heating and idle states of the sensing and control system, and facilitates an active over temperature detection that is independent of the temperature control loop. Temperature sensing also remains active during the over temperature condition.

The circuit configuration may comprise a common ground referenced heating/sensing system with a supply voltage switching to the tube circuit for heating control. An alternative approach is to utilise the supply voltage as both the heating and sensing source voltage and control heating by switching to 0V the tube circuit.

Figure 21:
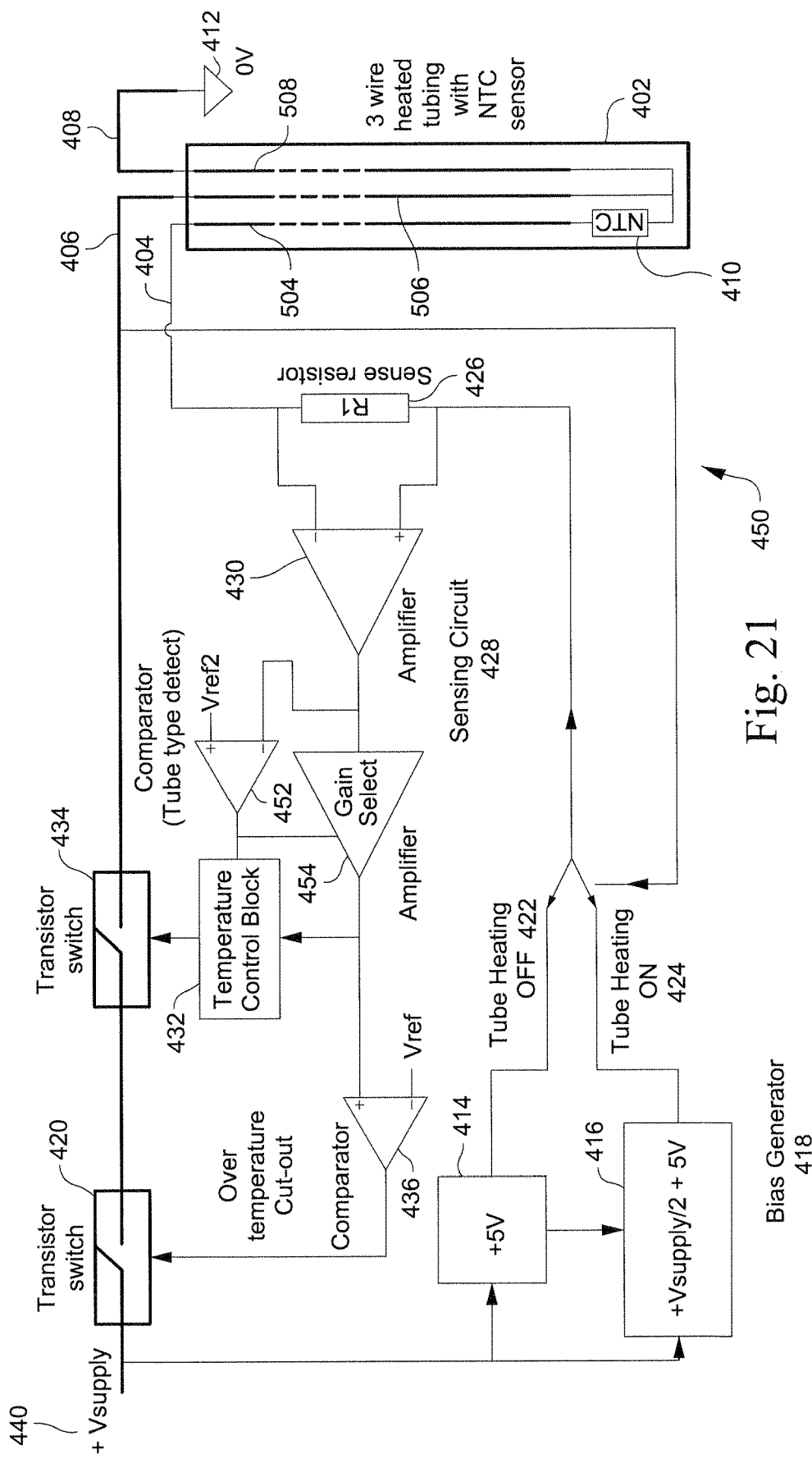
FIG. 21 schematically depicts a circuit according to still another sample embodiment that senses a temperature at the patient interface, detects a tube type, and provides active over temperature protection.
Figure 23:
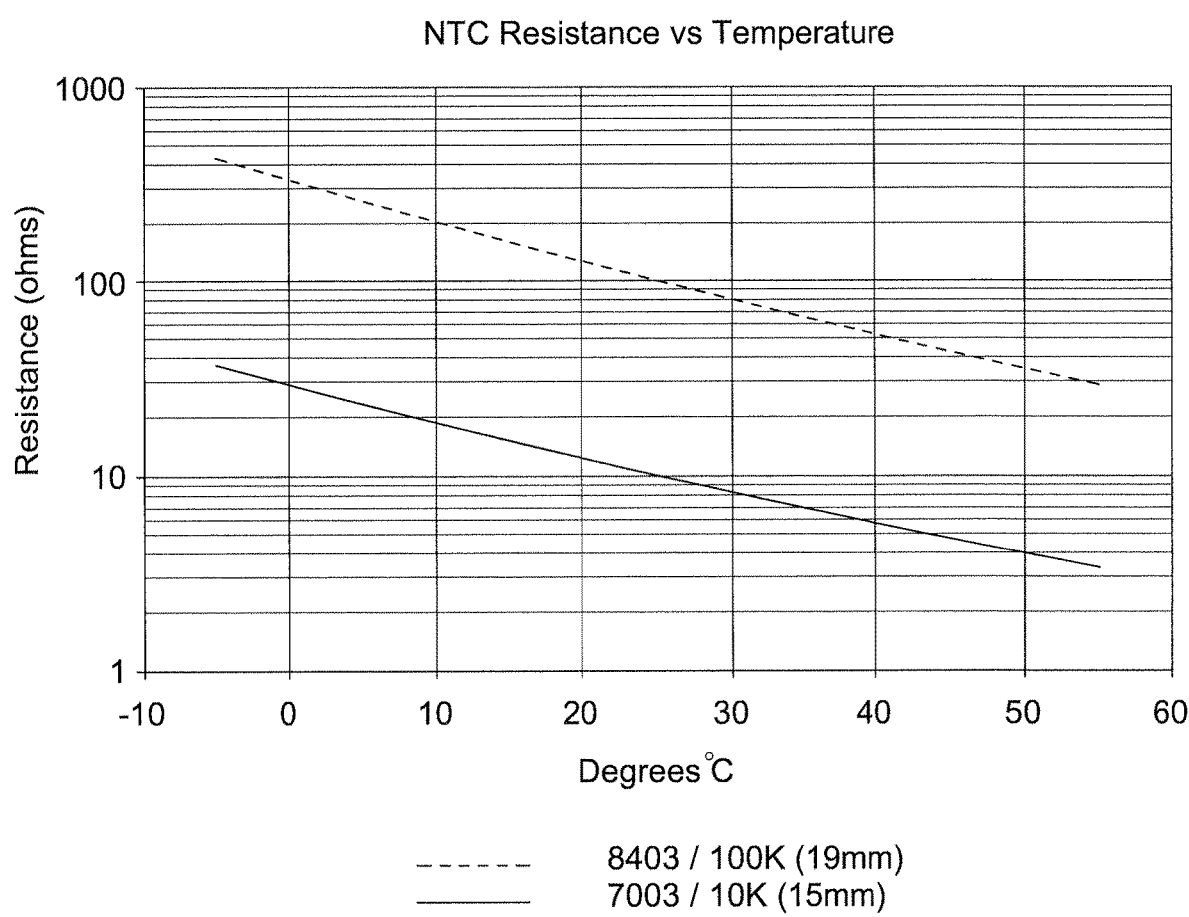
FIG. 23 schematically depicts a relationship between a resistance of a temperature sensor and temperature according to sample embodiments.

Heated Tube Control—Temperature Sensing with Tube Type Detection and Active Over Temperature Protection Referring to FIG. 21, a sensing and control circuit configuration 450 according to another sample embodiment allows for discrimination between different values of the temperature sensor (e.g. thermistor value as an indicator of tubing type) to permit changes in system performance to compensate for changes in the characteristics of the tube types (e.g. pressure drop versus bore/internal diameter). For each tube type used within the system there should not be an overlap in the resistances obtained from using the different thermistors within the specified operating temperature range of the heated tube, for example between 0° C. and 45° C., preferably between −5° C. and 50° C. For example, a 15 mm internal diameter heated tube may include a temperature sensor with a thermistor value of 100 kΩ and a 19 mm internal diameter heated tube may include a temperature sensor with a thermistor value of 100 kΩ. FIG. 23 shows the characteristic curves for each of these example thermistor values. This allows the thermistor resistance value (or sensed voltage) to be used to detect the type of heated tube being used in the system. Thus, any compensation for air path performance can be adjusted automatically (without user intervention) for each tube type, if required. It should be appreciated that more than two types of tubes may be detected in the system by using multiple comparator and gains. Detection of the tube type can also be used to adjust the amplifier gain and increase the amplitude of the temperature sense signal for a lower sensitivity (higher value NTC thermistor) circuit.

The signal gain may be adjusted so that the same over temperature threshold/circuit is used for different tube types (e.g. different internal diameters).

The circuit configuration 450 of FIG. 21 includes all the components shown in the circuit configuration 400 shown in FIG. 20 and the same numbers are used to identify the similar components. The circuit configuration 450 comprises an additional tube type detect circuit comprising a comparator 452 to compare the sensed voltage from amplifier 430 with a voltage reference $V_{ref2}$ that identifies a specific heated tube resistance value to identify if a first tube type (e.g. size) is attached to the system. If sensed voltage is equal to and/or greater than the voltage reference $V_{ref2}$ then the first tube type is determined as attached to the system and a gain is added via amplifier 454 to the sensed voltage so that the same voltage value is applied to the comparator 436 for the over-temperature control circuit. If the sensed voltage from amplifier 430 is not equal to and/or lower than the voltage reference $V_{ref2}$ a second tube type is determined as attached to the system and no gain is added to the sensed voltage. In this manner the same threshold voltage for the over temperature detection is used for both heated tube types. It should be appreciated that more than two types of tubes may be detected in the system by using multiple comparators and gains.

In an alternative embodiment the system may detect the different resistances of the different tube types in a similar manner but instead of adding a gain using amplifier 454 the comparator may use different reference voltages $V_{ref}$ for each of the different tube types.

Heated Tube Control—Temperature Sensing with Tube Type Detection, Active Over Temperature Protection, and Connect Fault Detection Extreme variations in the temperature sense signal can also be used to detect electromechanical faults in the tubing circuit or in the electrical connection of the tubing to the system. This is achieved with the window comparator shown in FIG. 22 which may comprise resistors R2, R3, R4 which are biased by a voltage, e.g. 5V. This provides a more reliable connect fault detection than current heated tube systems on the market that use over-current and current spark detection of fault sites.

Figure 22:
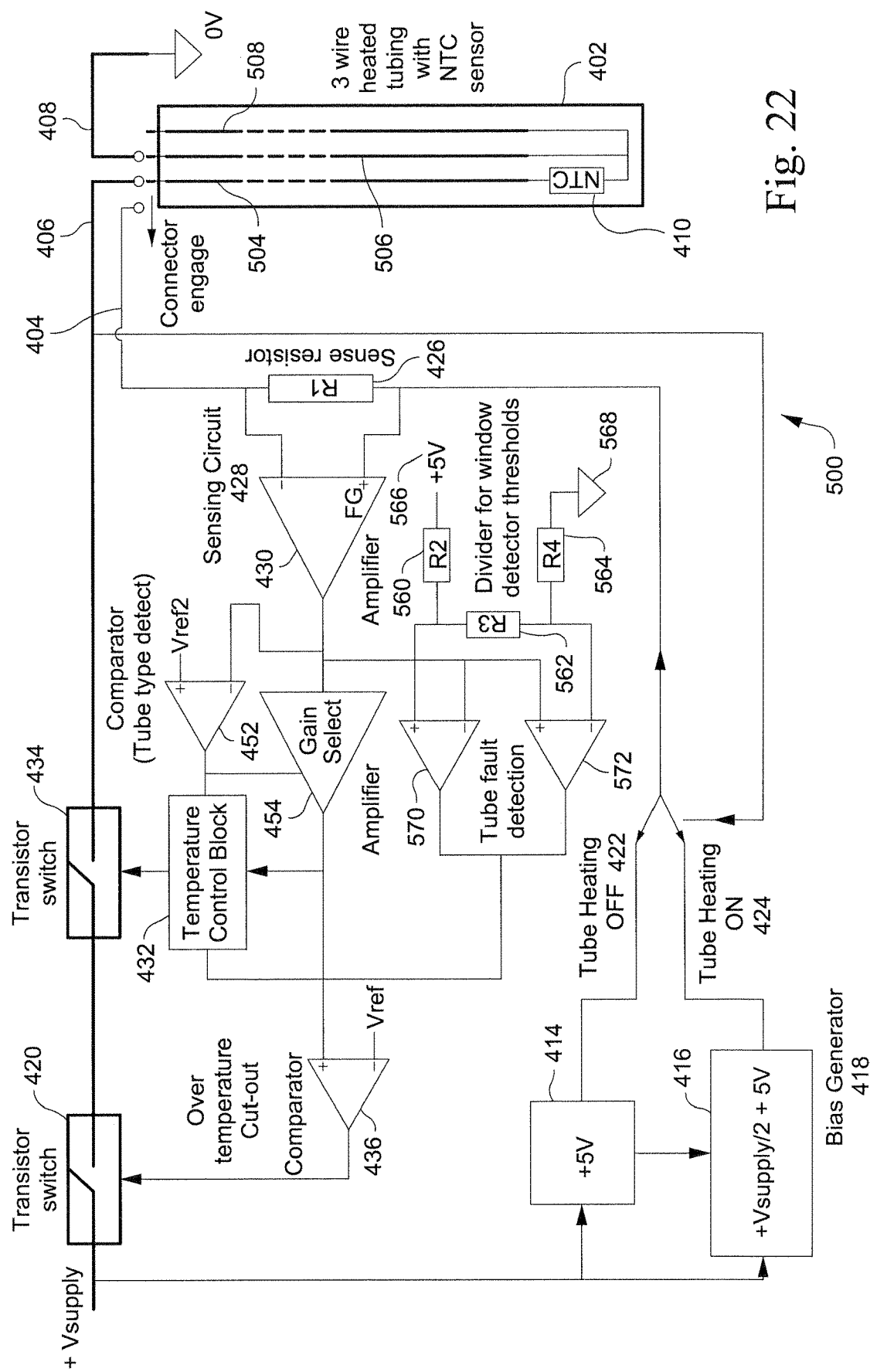
FIG. 22 schematically depicts a circuit according to yet another sample embodiment that senses a temperature at the patient interface, detects a tube type, provides active over temperature protection, and detects a connection fault.

The sensing and control circuit configuration 500 shown in FIG. 22 includes all the features shown in the circuit configuration 450 of FIG. 21 with like components identified with the same number. The circuit configuration 500 includes a tube fault detection circuit comprising three resistors 560, 562 and 564, that are used to set the window threshold of sensed voltages expected from a correctly working system. A source voltage 566, that is the same as that used in the bias generator 418, and a ground 568 are used to set the window thresholds of the sensed voltages. The comparators 570 and 572 compare the voltage received from the amplifier 430 with the window thresholds and if the sensed voltage is outside the expected range then a tube fault is detected and a signal is sent to the temperature control block 432 to open the transistor switch 434 to prevent power to the system.

The tube fault detection system is also able to detect the correct connection of the heated tube to the system. The control system has three connectors attached to the ends of wires 404, 406 and 408 that are adapted for connection with connectors on the ends of the three wires 504, 506 and 508 of the heated tube circuit 402. The connectors are arranged such that the last connectors to connect are those relating to the sensing wire 504. This ensures that if the heated tube is not correctly connected a fault will be detected in the control system as the voltage sensed by sense resistor 426 will be 0V. This fault detection system will detect faults such as short circuits, open circuits, wiring faults or connection faults.

It should be appreciated that in the three sample embodiments of the heated tube control circuits discussed above, the circuit may be configured to disable heating in the event of a fault in the temperature sensor that renders it open or short circuited. This feature may be provided as an additional safety measure, for example in the embodiments in which the circuit comprises includes the thermal fuse or in the embodiments in which the thermistor is provided to a fixture within the cuff.

Heating Plate Control—Overheating Prevention

The PAP system may operate according to various control algorithms, for example as disclosed in U.S. Patent Application Publication 2009/0223514 A1. The ambient humidity sensor (e.g., the temperature sensor) provided in the humidifier may be close to the heating plate of the humidifier and the operation of the ambient humidity sensor(s) may be affected by the heating plate. For example, the heating plate temperature sensor may be an NTC sensor that experiences "drift," i.e., the resistance of the NTC sensor rises above the specification for the NTC sensor. The drift causes the NTC sensor to detect a temperature lower than the actual temperature of the humidifier heating plate. In order to prevent the heating plate from being heated to an unsafe temperature, it is possible to provide a control algorithm that is designed to prevent heating of the heating plate when the temperature measured by the heating plate temperature sensor and the temperature measured by the humidity sensor, when considered together, are regarded as implausible.

Figure 24:
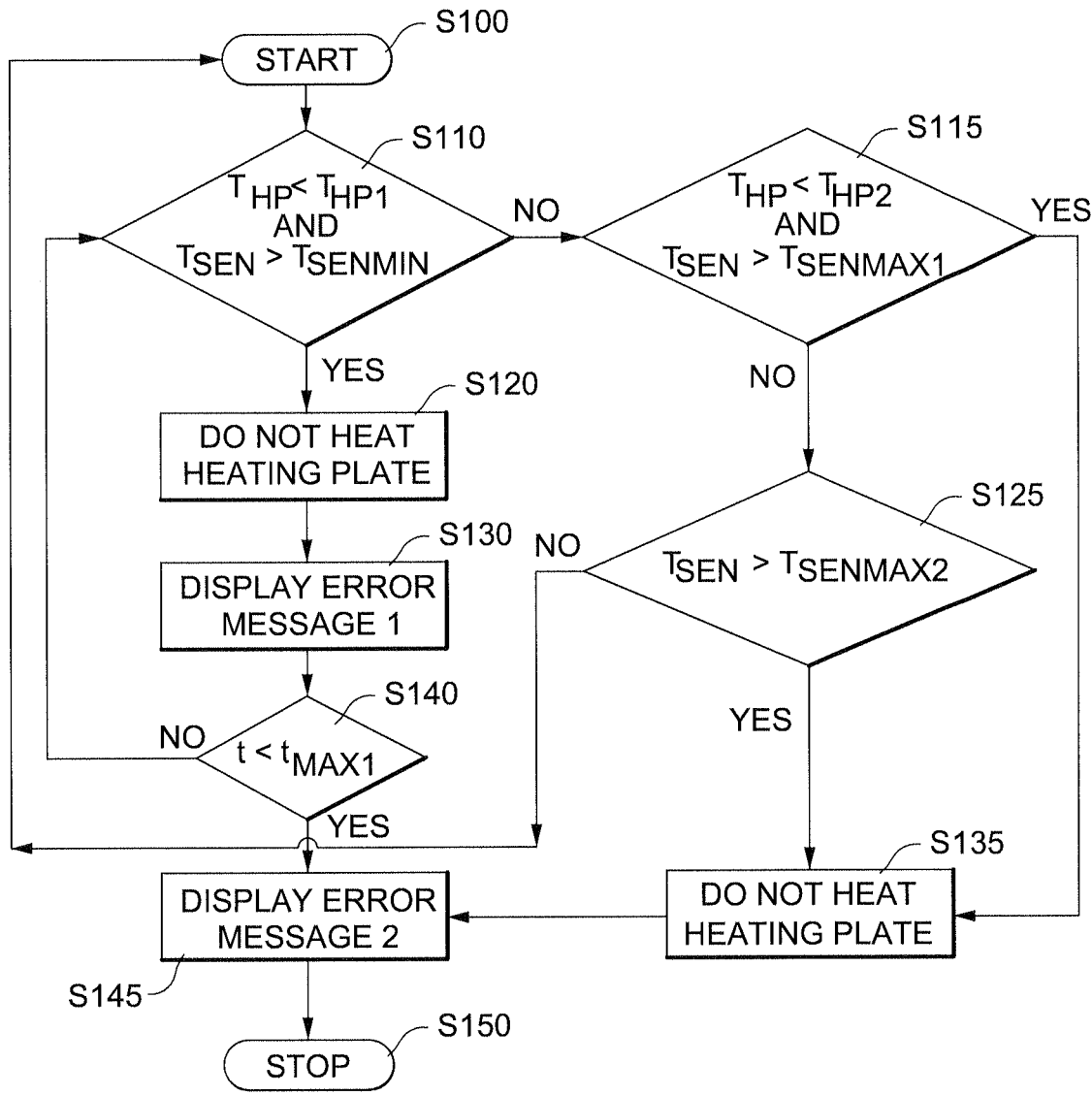
FIG. 24 schematically depicts an algorithm for controlling the heating plate of the humidifier according to a sample embodiment.

Referring to FIG. 24, a control algorithm may be provided to prevent overheating of the humidifier heating plate. The control algorithm may be run concurrently with any of the PAP system control algorithms disclosed in U.S. Patent Application Publication 2009/0223514 A1. The control algorithm starts in S100 and proceeds to S110. In S110 it is determined if the heating plate temperature $T_{HP}$ is lower than a first predetermined heating plate temperature $T_{HP1}$ and whether the sensed temperature $T_{SEN}$ detected by the humidity sensor is higher than a minimum sensed temperature $T_{SENMIN}$. The first predetermined heating plate temperature $T_{HP1}$ may be the minimum temperature of the humidifier heating plate that is plausible. For example, very cold water may be placed in the humidifier, but ice should not be. So a first predetermined heating plate temperature $T_{HP1}$ may be, for example, between about 0° C. and 4° C., such as about 2° C. The minimum sensed temperature $T_{SENMIN}$ may be a minimum ambient temperature at which the PAP system is recommended to be used. For example, the minimum sensed temperature $_{SENMIN}$ may be between about 3° C. and 8°, such as about 5° C.

If the temperature of the heating plate $T_{HP}$ is lower than the first predetermined heating plate temperature $T_{HP1}$ and the sensed temperature $T_{SEN}$ is higher than the minimum sensed temperature $T_{SENMIN}$ (S110: Yes), the control proceeds to S120 and prohibits heating the humidifier heating plate. It is noted that the answer to both queries in S110 must be YES to proceed to S120. If the answer to either query is NO, then the process moves to S115, which is described in detail below. An acknowledgeable error message ERROR MESSAGE 1 is displayed in S130. For example, the display 4 may display "HUMIDIFIER_THERMISTOR_OPEN." The user or operator may acknowledge the error message, for example by pressing one of the inputs 6 and/or the push button dial 8. After the error message is displayed, the control proceeds to S140 and it is determined whether the time t that the PAP system has been operating under the conditions checked in S110 is less than a first maximum time $t_{MAX1}$. The first maximum time $t_{MAX1}$ may be, for example, 15 minutes. If the conditions checked in S110 have occurred for more than the first maximum time (S140: Yes), the control proceeds to S145 and a second error message ERROR MESSAGE 2 is displayed on the display of the PAP system. The control then proceeds to S150 and operation of the PAP system is stopped.

The second error message ERROR MESSAGE 2 may be "HUMIDIFIER_HW_OVERPROTECTION_FAILURE."

The second error message ERROR MESSAGE 2 can not be acknowledged by the user or operator. The second error message ERROR MESSAGE 2 may only be removed by the user or operator by clearing the PAP system with a power cycle, i.e., by turning the PAP system off and then back on.

If the conditions checked in S110 have not occurred for longer than the first maximum time (S140: No), the control returns to S110 to check the heating plate temperature $T_{HP}$ and the sensed temperature $T_{SEN}$.

If the heating plate temperature $T_{HP}$ is higher than the first predetermined heating plate temperature $T_{HP1}$ and/or the sensed temperature $T_{SEN}$ is lower than the minimum sensed temperature $T_{SENMIN}$ (S110: No), i.e. either or both of the queries output NO, the control proceeds to S115 and determines whether the heating plate temperature $T_{HP}$ is lower than a second predetermined heating plate temperature $T_{HP2}$ and whether the sensed temperature $T_{SEN}$ is higher than a first maximum sensed temperature $T_{SENMAX1}$. The first maximum sensed temperature $T_{SENMAX1}$ and the second predetermined heating plate temperature $T_{HP2}$ may be temperatures that are anticipated during operation of the PAP system. For example, it may be anticipated that whenever the sensed temperature is above 40° C., then the heating plate temperature will be above 25° C.

If the heating plate temperature $T_{HP}$ is lower than the second predetermined heating plate temperature $T_{HP2}$ and the sensed temperature $T_{SEN}$ is higher than the first maximum sensed temperature $T_{SENMAX1}$ (S115: Yes), the control proceeds to S135 and heating of the humidifier heating plate is prohibited. It is noted that the output of both queries in S115 must be YES to proceed to S135. If the output of either query is NO, then the process moves to S125, which is described in more detail below. The control then proceeds from S135 to S145 and the second error message ERROR MESSAGE 2 is displayed. The control then stops the PAP system in S150.

If the heating plate temperature $T_{HP}$ is higher than the second predetermined heating plate temperature $T_{HP2}$ and/or the sensed temperature $T_{SEN}$ is lower than the first maximum sensed temperature $T_{SENMAX1}$ (S115: No), i.e. either or both of the queries output NO, the control proceeds to S125 and it is determined if the sensed temperature $T_{SEN}$ is higher than a second maximum sensed temperature $T_{SENMAX2}$. The second maximum sensed temperature $T_{SENMAX2}$ may be higher than the first maximum ambient temperature $T_{SENMAX1}$ and may be an upper limit on the temperature detected by the humidity sensor regardless of the detected heating plate temperature. For example, $T_{SENMAX2}$ may be between about 45° C. and 55° C., for example about 50° C. as this temperature may clearly indicate that the humidifier is overheated (e.g., irrespective of the heating plate temperature), and may provide sufficient margin for normal operation even in 35° C. ambient. The second higher maximum sensed temperature $T_{SENMAX2}$ is an additional check to ensure that the humidity sensor is not too hot. This check is done every time one of the queries in S115 outputs NO. It is noted that if the sensed temperature is lower than the first maximum sensed temperature $T_{SENMAX1}$ then the sensed temperature should also be below the second maximum sensed temperature $T_{SENMAX2}$ if the second maximum sensed temperature $T_{SENMAX2}$ is higher than the first maximum sensed temperature $T_{SENMAX1}$. Thus this check is particularly useful when the heating plate temperature $T_{HP}$ is higher than the second predetermined heating plate temperature $T_{HP2}$.

If the sensed temperature $T_{SEN}$ is lower than the second maximum ambient temperature (S125: No), the control returns to S100 and starts again.

It should be appreciated that the first and second error messages may be the same. For example, the display 4 of the PAP system may display "HUMIDIFIER FAULT" for both the first and second error messages. However, the first error message represents a recoverable system error and is acknowledgeable by the user or operator and may be cleared, whereas the second error message represents a non-recoverable system error and can not be acknowledged and cleared by the user or operator except through a power cycle (turning the PAP system off and then back on).

Heating Plate Configuration

Figure 29:
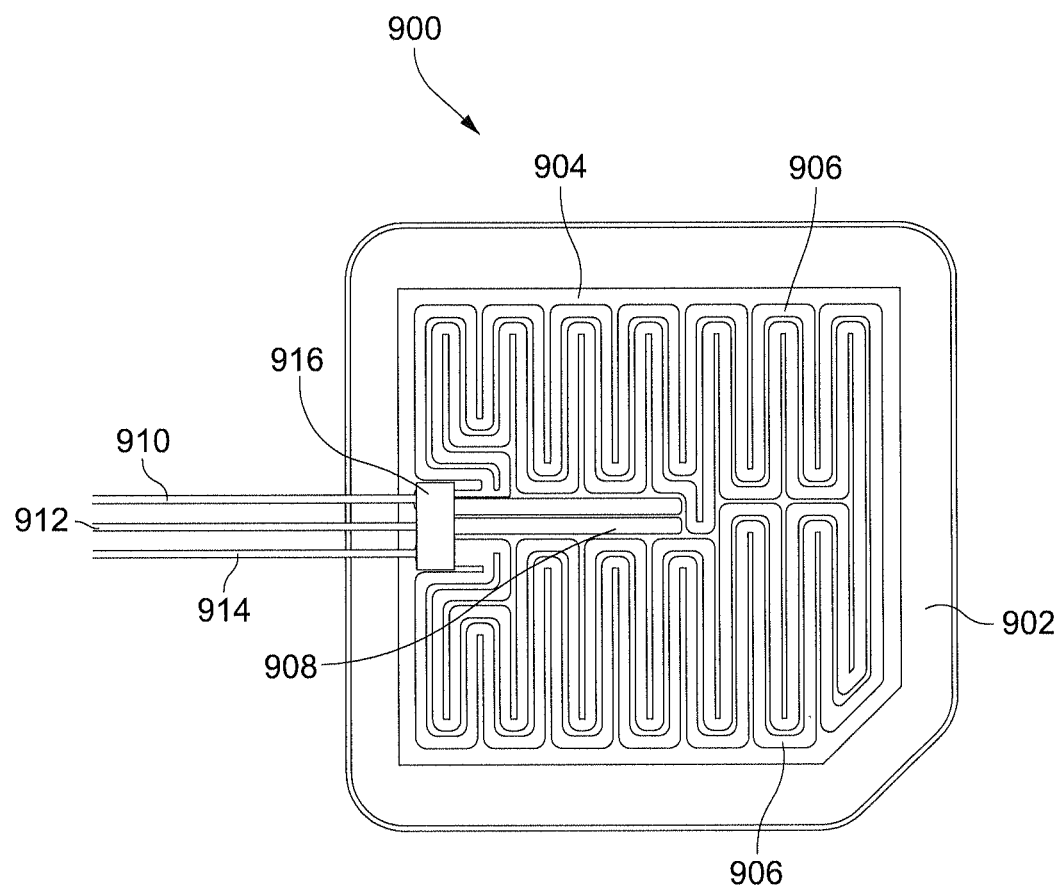
FIG. 29 schematically depicts a humidifier heating plate according to a sample embodiment.

Referring to FIG. 29, the humidifier heating plate 900 may comprise a plate 902 formed of a heat conducting material. The heat conducting plate 902 may be made of, for example, metal, such as a nickel chrome alloy or anodized aluminum. A heating element 906 may be provided on the heat conducting plate 902. The heating element 906 may be formed from a resistive film, and may be formed by, for example, stamping or etching a resistive foil. An insulating layer 904 may cover the heating element 906. For stamping, the resistive film 906 is inserted between two insulating films 904. For etching, the resistive film 906, with an attached insulating film 904 on one of its sides, is covered by a second insulating film 904. The insulting film 904 may be formed of, for example, KAPTON®.

The heating plate 900 of the humidifier may further comprise a thermistor 908. The thermistor 908 may also be formed from a resistive film. The thermistor may be cut, stamped, or etched from a suitable resistive foil, for example, a metal foil, similar to the heating element 906. A plurality of wires 910, 912, 914 may be attached to the heating element 906 and the thermistor 908. The wires 910, 912, 914 may be connected to the heating element 906 and the thermistor 908 by, for example, solder 916.

Figure 30:
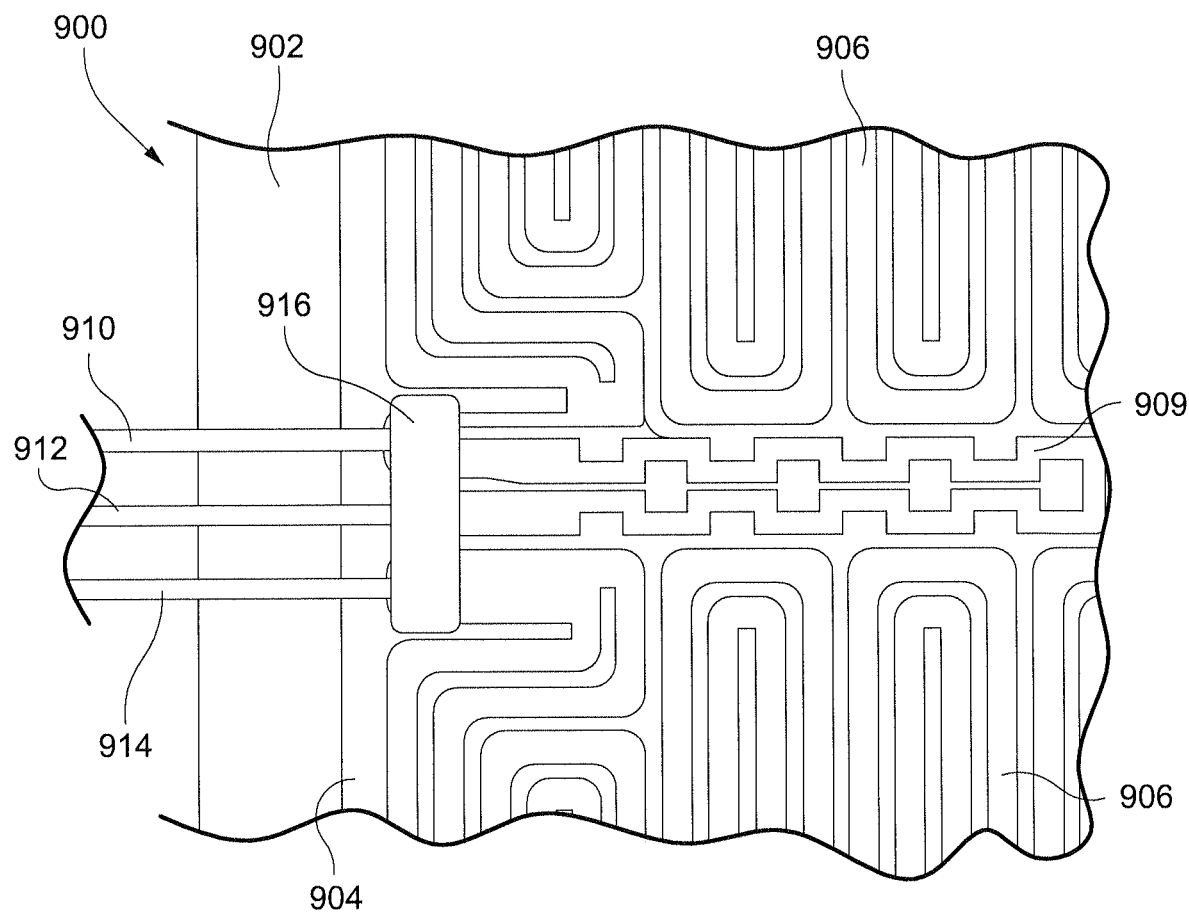
FIGS. 30 and 31 schematically depict a humidifier heating plate according to another sample embodiment.

Referring to FIG. 30, a humidifier heating plate 900 according to another sample embodiment may comprise a thermistor 909 that has a zig-zag shape. The thermistor 909 may be integrally formed with the heating element 906 by forming the thermistor 909 and the heating element 906 from a suitable resistive film, e.g. a resistive metal foil. Two insulating films 904 insulate the top and bottom surfaces of the heating element 906 and the thermistor 909. The integrated thermistor 909 may be excited by a constant current so the resistance changes with temperature are converted into a voltage that can be amplified and used by the humidifier heating control circuit.

Figure 31:
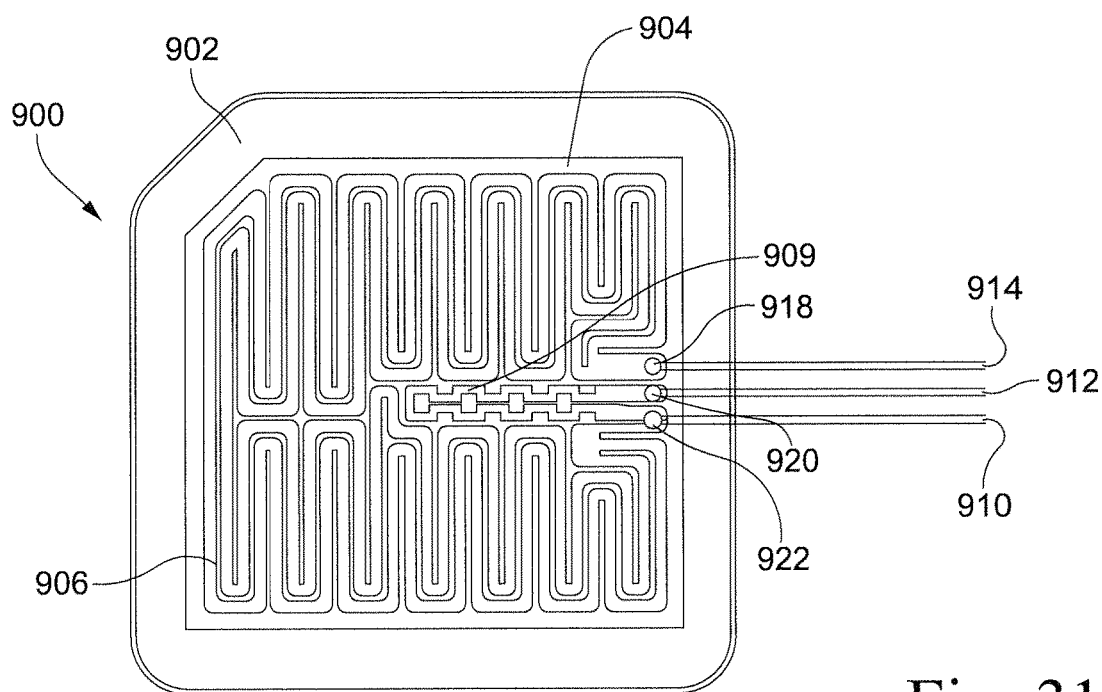

Referring to FIG. 31, a humidifier heating plate 900 according to another sample embodiment may comprise a heating element 906 formed of a resistive film formed of a first material and a thermistor 909 formed of a resistive film of a second material different from the first material. The second material that forms the thermistor 909 may have a high resistance than the first material. The wires 910, 912, 914 may be ultrasonically welded at points 918, 920, 922 to the heating element 906 and the thermistor 909. The connection point 922 connects the wire 910 to both the heating element 906 and the thermistor 909.

Figure 32:
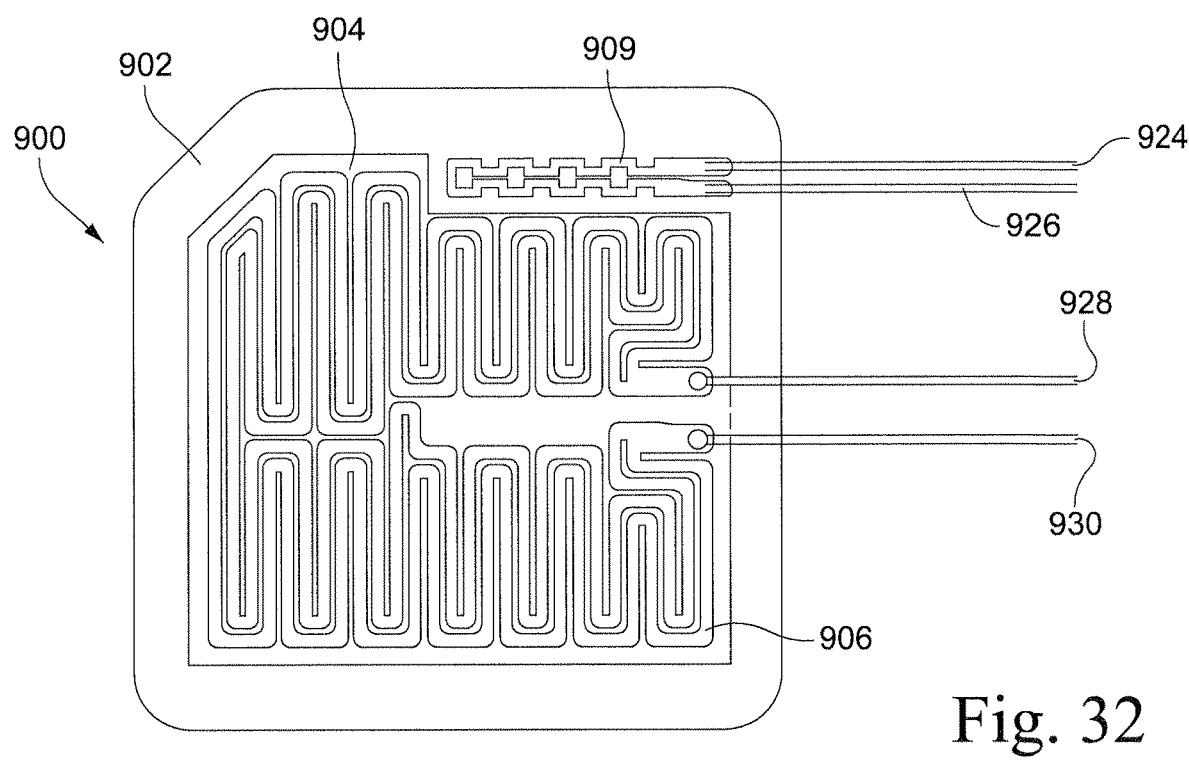
FIG. 32 schematically depicts a humidifier heating plate according to yet another sample embodiment.

Referring to FIG. 32, a humidifier heating plate 900 according to another sample embodiment comprises a heating element 906 covered by an insulating layer 904. A thermistor 909 is provided separate from the heating element 906 and the insulating layer 904. It should be appreciated that the thermistor 909 may also be insulated by separate insulating films. Wires 928, 930 connect the heating element 906 to the power supply and humidifier heating control circuit and wires 924, 926 connect the thermistor 909 to the power supply and humidifier heating control circuit.

Figure 33:
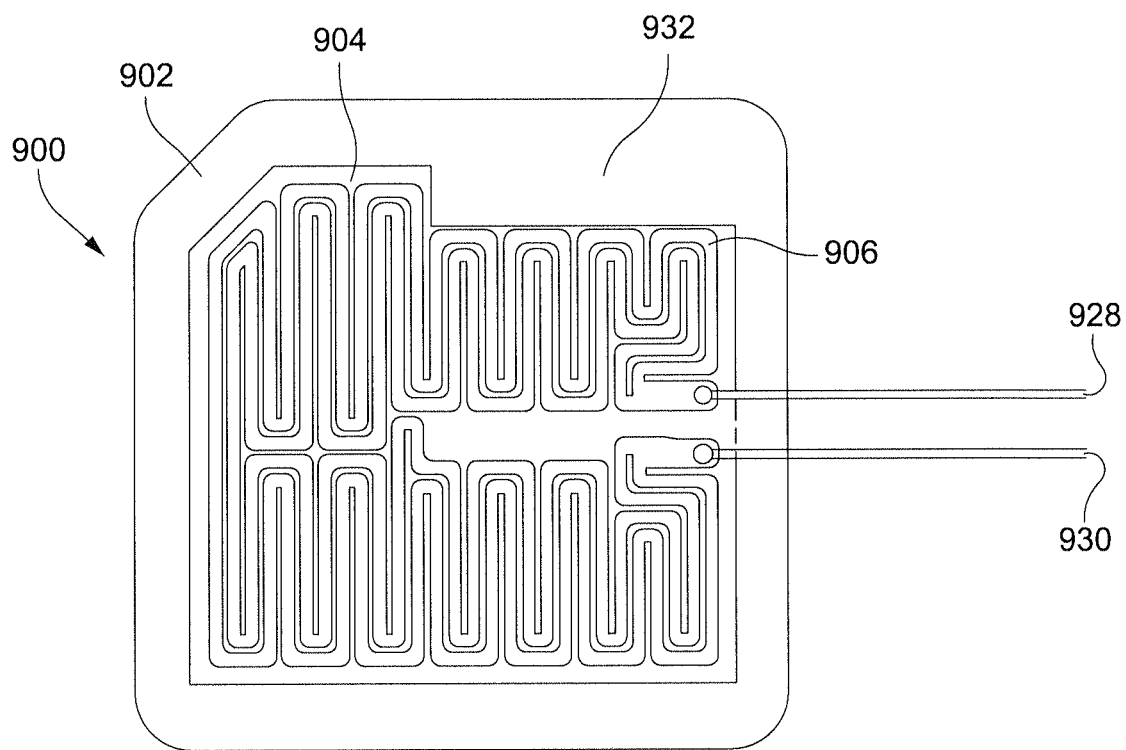
FIG. 33 schematically depicts a humidifier heating plate according to a still further sample embodiment.

Referring to FIG. 33, a humidifier heating plate 900 according to a further sample embodiment includes a heating element 906 insulated by two insulating films 904. The heat conducting plate 902 includes a free area 932 which may accommodate at least one electric circuit that may be used to perform temperature measurements without the use of a thermistor. For example, if the heater element 906 is made of resistive film of a material whose resistance increases with temperature, the electric circuit can measure the heater plate temperature by measuring the resistance of the heating element.

The provision of an integrally formed heating element and thermistor, as shown for example in FIG. 30, overcomes a problem experienced with discrete thermistors that may tend to crack when used to measure temperature in the humidifier heating plate. The provision of an integrally formed heating element and thermistor also provides improved resistance to mechanical shocks and provides more reliable humidifier temperature control. Integrally forming the heating element and the thermistor also simplifies the assembly process as there is no need to solder a discrete thermistor to the humidifier heating plate.

Heated Tube Control—Overheating Prevention

The NTC sensor in the heated tube may also experience drift. A drift in the resistance of the temperature sensor in the heated tube may cause the temperature sensor to detect a temperature lower than the actual temperature of the heated tube. This could lead the PAP system to overheat the heated tube.

Figure 25:
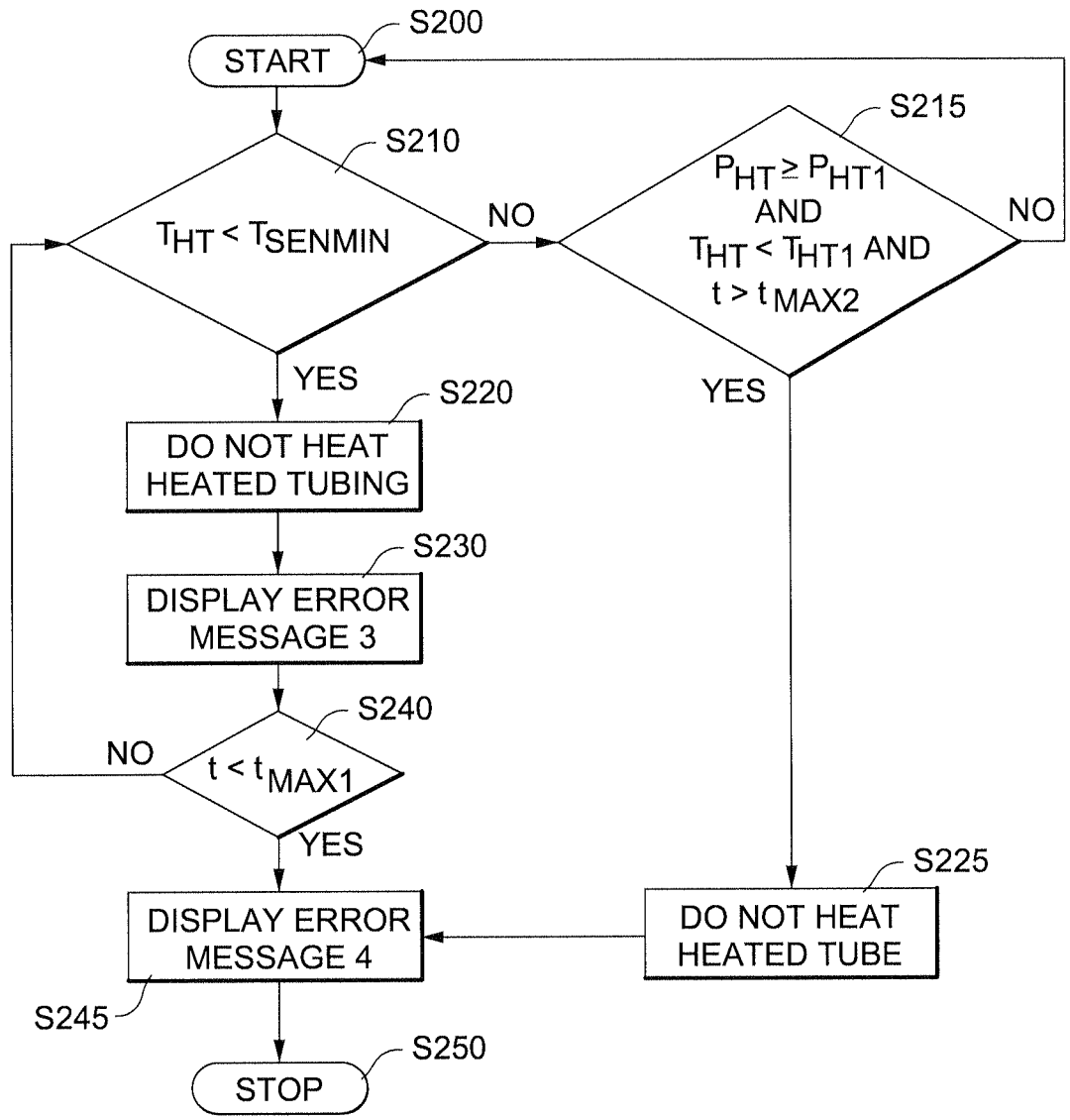
FIG. 25 schematically depicts an algorithm for controlling the heated tubing according to yet another sample embodiment.

Referring to FIG. 25, a control algorithm may be provided to prevent overheating of the heated tube. The control algorithm may be run concurrently with any of the PAP system control algorithms disclosed in U.S. Patent Application Publication 2009/0223514 A1 and with the heating plate control algorithm of FIG. 24. The control starts in S200 and proceeds to S210. In S210 it is determined if the heated tube temperature $T_{HT}$ is lower than the minimum sensed temperature $T_{SENMIN}$. If the temperature of the heated tube $T_{HT}$ is lower than the minimum ambient temperature $T_{SENMIN}$ (S210: Yes), the control proceeds to S220 and an acknowledgeable error message ERROR MESSAGE 3 is displayed in S230. For example, the display 4 may display "HEATED_TUBE_CURRENT-TRIP." The user or operator may acknowledge the error message, for example by pressing one of the inputs 6 and/or the push button dial 8. After the error message is displayed, the control proceeds to S240 and it is determined whether the time t that the PAP system has been operating under the conditions checked in S210 is less than the first maximum time $t_{MAX1}$. If the conditions checked in S210 have occurred for more than the first maximum time (S240: Yes), the control proceeds to S245 and a fourth error message ERROR MESSAGE 4 is displayed on the display of the PAP system. The control then proceeds to S250 and operation of the PAP system is stopped.

The fourth error message ERROR MESSAGE 4 may be "HEATED_TUBE_HW_OVERPROTECTION_FAILURE.". The fourth error message ERROR MESSAGE 4 can not be acknowledged by the user or operator. The fourth error message ERROR MESSAGE 4 may only be removed by the user or operator by clearing the PAP system with a power cycle.

If the conditions checked in S210 have not occurred for longer than the first maximum time (S240: No), the control returns to S210 to check the heated tube temperature $T_{HT}$ against the minimum sensed temperature $T_{SENMIN}$.

If the heated tube temperature $T_{HT}$ is higher than the minimum sensed temperature $T_{SENMIN}$ (S210: No), the control proceeds to S215 and determines whether the power supplied to the heated tube $P_{HT}$ is greater than or equal to a first predetermined heated tube power $P_{HT1}$, whether the detected temperature of the heated tube $T_{HT}$ is lower than a first predetermined heated tube temperature $T_{HT1}$ and whether an elapsed time t is less than a second maximum time $t_{MAX2}$. If the power $P_{HT}$ supplied to the heated tube is greater than or equal to the first predetermined heated tube power $P_{HT1}$, the detected temperature $T_{HT}$ of the heated tube is less than the first predetermined heated tube temperature $T_{HT1}$, and the elapsed time is greater than the second maximum time $t_{MAX2}$ (S215: Yes), i.e. all three queries must output YES in S215, the control proceeds to S225 and the heated tube is prevented from heating. The control then proceeds to S245 and the fourth error message ERROR MESSAGE 4 is displayed. The control then stops operation of the PAP system in S250.

If the power $P_{HT}$ supplied to the heated tube is less than the first predetermined heated tube power $P_{HT1}$, the detected temperature $T_{HT}$ of the heated tube is greater than the first predetermined heated tube temperature $T_{HT1}$, and/or the elapsed time is less than the second maximum time $t_{MAX2}$ (S215: No), i.e. one or more of the three queries in S215 outputs NO, the control returns to S200 and starts over.

It should be appreciated that the third and fourth error messages may be the same. For example, the display 4 of the PAP system may display "TUBE FAULT" for both the third and fourth error messages. However, the third error message represents a recoverable system error and is acknowledgeable by the user or operator and may be cleared, whereas the fourth error message represents a non-recoverable system error and can not be acknowledged and cleared by the user or operator except through a power cycle (turning the PAP system off and then back on). It should also be appreciated that the third and fourth error messages may be the same as the first and second error messages, e.g. "HUMIDIFIER FAULT."

As noted with respect to FIG. 23, a 15 mm internal diameter heated tube may include a temperature sensor with a thermistor value of 10 lΩ and a 19 mm internal diameter heated tube may include a temperature sensor with a thermistor value of 100 kΩ. The PAP system may be operated over a recommended temperature range. For example, the lowest recommended sensed (ambient) temperature at which the PAP system may be operated is 5° C., and the highest recommended sensed temperature at which the PAP system may be operated is 35° C. If the system is stored at the lowest recommended ambient temperature, e.g. 5° C., it is expected that the system will warm to above the lowest recommended ambient temperature in about 15 minutes. Over the recommended temperature range, the resistance values of the NTC temperature sensor in the heated tube will vary. For example, the temperature sensor in a 15 mm internal diameter heated tube may have a resistance ranging from about 8 kΩ to 28 kΩ and the temperature sensor in a 19 mm inner diameter heated tube may have a resistance ranging from about 80 kΩ to 750 kΩ. These ranges can be reduced by the heated tube control shown in FIG. 25, in particular by the steps S210, S220, S230, S240, S245 and S250. If the temperature of the heated tube is below the lowest recommended sensed (ambient) temperature (i.e. $T_{SENMIN}$) for operation of the PAP system, the control prevents heating of the heated tube. If this condition persists for more than 15 minutes (i.e. $t_{MAX1}$), the control stops the PAP system and displays an unrecoverable error message (i.e. ERROR MESSAGE 4). Control of the heated tube in this manner reduces the resistance range at which the PAP system can heat the heated tube. For example, the 15 mm inner diameter heated tube may be heated across a resistance range of about 8 kΩ to 23 kΩ, and the 19 mm inner diameter heated tube may be heated across a resistance range of about 80 kΩ to 250 kΩ.

Thermistor failures may be categorized by: (i) those that respond proportionally (negatively) to temperature, such as an NTC; (ii) those that carry a fixed resistance in series with the NTC element; and (iii) those that respond positively to temperature, i.e. increasing resistance as the temperature rises. Of course, this is a spectrum for which there may be mixed behaviour.

A 25° C. temperature rise is needed to change the resistance of a standard NTC from 23 kΩ to 8 kΩ or from 250 kΩ to 80 kΩ. Therefore an NTC at the extreme of 23 kΩ or 250 kΩ at 30° C. might need a 25° C. temperature rise to get to 8 kΩ or 80 kΩ respectively. A 25° C. rise on 30° C. is 55° C., at which temperature the tubing has not reached its softening temperature.

A thermistor with a fixed offset pushing its resistance outside the operating ranges will cause the PAP system to not heat the heated tube. A more subtle case where the resistance is within the operating range is more difficult to detect. If the resistance rises with temperature, the PAP system will interpret this as cooling. As in the case with a fixed offset, the resistance of the thermistor will either be pushed outside the operating range for heating, or it will be the subtle case that is more difficult to detect.

To detect the subtle cases, a condition that occurs when the heated tube temperature is unresponsive to significant applied power may be observed. The PAP system may be designed to distribute power between the heating plate of the humidifier and the heated tube. For example, the heated tube may have priority over, for example, 60% of the available power. In the embodiments described in FIGS. 20-22, 36 W are available to the heated tube. The criteria for the decision in S215 of the control algorithm of FIG. 25 may be set based on tests conducted at the extremes of the recommended ambient temperature operating range of the PAP system. At the minimum recommended sensed (ambient) operating temperature of 5° C. and supplying full power to the heated tube, the temperature of the heated tube rose above 15° C. within 3 minutes. A 15° C. temperature increase corresponds to 15 kΩ for a 15 mm tube and 150 kΩ for a 19 mm tube. Therefore, if the temperature of the heated tube has not risen above 15° C. (i.e. $T_{HT1}$) after 3 minutes (i.e. $t_{MAX2}$) of 36 W (i.e. $P_{HT1}$), the control can stop heating the heated tube before the heated tube is in danger of being damaged. It should be appreciated that other times and corresponding temperature measures may be used.

Heated Tube—Electro-Pneumatic Connection

The tube electrical connection may be made via a bayonet style connector that operates on an axis co-aligned with the tube pneumatic fitting, for example as described herein in relation to FIGS. 8-17. The three contacts may engage sequentially as shown in FIG. 22 with the sensor contact remaining disconnected until full engagement of the connector is made. The heating circuits are inactive until the tube presence is established. The signals may be arranged such that the temperature sensor line is engaged last of the three conductors. The circuit does not recognise that a tube is connected until this line is connected. The ground line is the first line engaged and therefore the most accessible conductor. It is also the line least likely to affect the operation of the circuit if it is inadvertently touched by the user.

Although the tube size (e.g. internal diameter) has been disclosed as being detected automatically upon connection, it should be appreciated that it is also possible that the tube size may be selected manually by the user through the user interface of the humidifier and/or the flow generator.

The heated tube electrical circuit allows lower profile tubing and cuff mouldings. A single assembly operation completes both the pneumatic and electrical connections between the tubing and the humidifier outlet which makes treatment/therapy easier to administer. Automatic adjustment of system performance with different tube types reduces, or eliminates, the need for clinician/patient adjustment of system settings.

The simpler tubing configuration is less expensive to manufacture. Using active over temperature detection reduces the cost of the tubing assembly and parts by eliminating the mechanical thermal cut-out switch. A three wire tubing circuit provides output end temperature sensing using the heating circuit as part of the sensing circuit. Thus, the overall tubing circuit has fewer connections and components and is simpler and less expensive to manufacture. The simpler tubing circuit is easier to manufacture and makes automation more easily achievable.

The simpler tubing configuration allows for higher volume production. The electronic circuit uses standard components readily available for high production volumes.

It should be appreciated that the heated tube may optionally include a thermal cut-out fuse/switch, for example if a stand-alone heated tube with a separate power supply is used. Such a thermal cut-out fuse/switch is disclosed in, for example, U.S. Patent Application Publication 2008/0105257 A1. It should also be appreciated that such a thermal cut-out/fuse, and/or other circuit configurations disclosed herein, may be provided on a printed circuit board provided in the cuff of the heated tube.

Power Supply for Patient Interface

Figure 26:
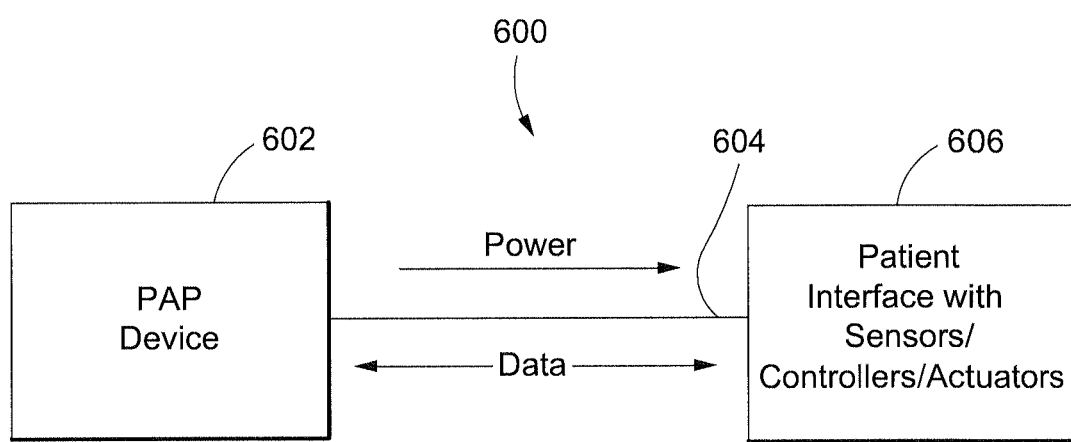
FIG. 26 schematically depicts a PAP system with a Powered Patient Interface according to a further sample embodiment.

Referring to FIG. 26, a sample embodiment of a PAP system 600 comprises a PAP device 602 connected to a patient interface 606. The PAP device 602 may be a flow generator or a flow generator connected to a humidifier. The PAP device 602 may be connected to the patient interface 606 via a conduit 604 (e.g. a heated tube as described herein). The conduit 604 provides for the transfer of power (e.g., electrical energy) from the PAP device 602 to the patient interface 606. Additionally, conduit 604 may be utilized to transfer data between the PAP device 602 and the patient interface 606. The data transferred from the patient interface 606 to the PAP device 602 may include, for example, information on various aspects of the patient interface, commands to the patient interface, or a combination thereof.

As discussed above, the patient interface 606 may include various sensors. The sensors may include, for example, a temperature sensor, a humidity sensor, a flow and pressure sensor, a microphone (e.g. voice), a noise cancellation sensor, a G force sensor (to allow the determination of whether a patient wearing the patient interface is laying face down, sitting up, etc), motion sensing for alternative (to flow) breath detection, a gagging detection sensor, a pulse oximeter, a particulates detector sensor, etc. In addition to the sensing functionality provided by the sensors, the sensors may also employ various techniques for alerting a user. For example, a sensor may include an LED that changes colour based on the particular property that is being sensed. Alternatively, or in addition to, a sensor may include a speaker that may be used to alert a user based on a reading from a sensor. Such speakers may also be used in conjunction with a microphone to create an "anti-noise" signal to cancel out surrounding noise.

In addition to the sensors provided on the patient interface 606, various controllers may also be provided to the patient interface 606. Such controllers may include, for example, actuators that directly humidify the patient interface, an active vent, a speaker or alarm, a noise cancellation control, vibration control (e.g., to signal a patient to wakeup), lamps for light therapy, etc. It should also be appreciated that the patient interface may include manual switches, e.g. dials, and/or controls that the patient or clinician may operate to control the system.

The conduit 604 may use one wire to carry both data and power between the PAP device 602 and the patient interface 606. Alternative embodiments, however, may utilize multiple wires to carry data and/or power between the PAP device 602 and the patient interface 606.

In further embodiments, the conduit that carries the power and data between the PAP device and the patient interface may utilize a non-heated tube. In yet further embodiments, the transmission of data over a link between the PAP device and the patient interface may be facilitated by utilizing CAN (Controller Area Network) or LIN (Local Interconnect Network) buses. Such buses may be utilized to create alternative embodiments of circuits to read data from sensors and operate controllers. In still further embodiments, an optical and/or transformer isolation may be provided for the link.

A patient interface with sensors and/or controllers may provide a PAP device with an ability to control an active vent of the patient interface. This may facilitate improved patient expiratory release. This control may lead to reduced flow generator and blower sizes as the corresponding vent flow is reduced. In turn this may create lower power usage, longer battery life, smaller sized PAP devices, smaller sized tubes (e.g., 10 mm), smaller sized patient interfaces, and may reduce the overall noise of the entire system and/or improve patient comfort.

Power Supply for Patient Interface System—Circuit for PAP Device

Figure 27:
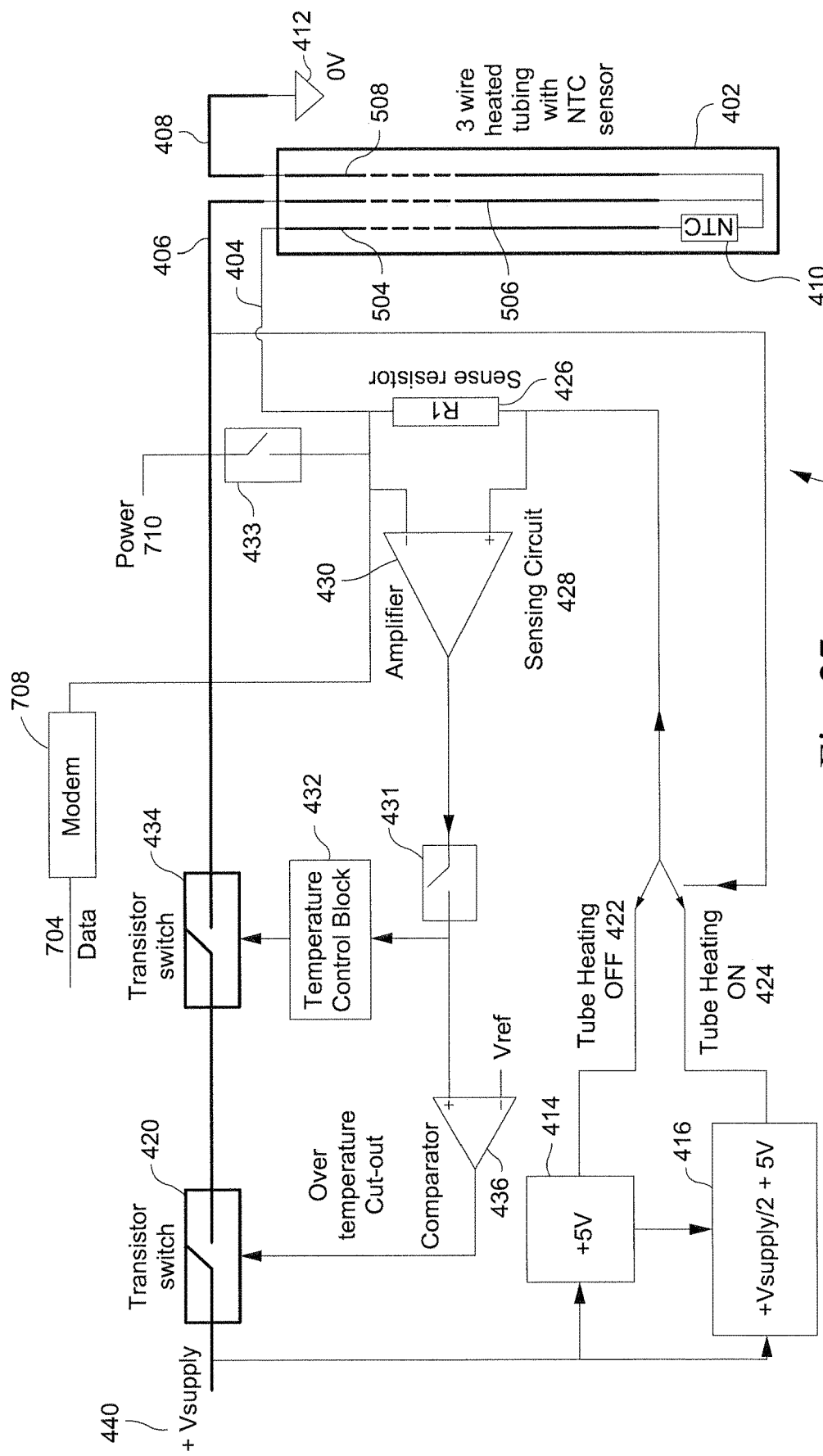
FIG. 27 schematically depicts a circuit according to yet another sample embodiment that facilitates communication of data and power out of the circuit.

Referring to FIG. 27, a sample embodiment of a circuit 700 that facilitates the transfer of power and data from a PAP or humidifier device to a patient interface is shown.

The circuit 700 may include components of the sensing and control circuit 400 shown in FIG. 20. The same reference numbers are used to identify similar components. In addition to those features found in circuit 400, circuit 700 may include a modem 708. The modem 708 may provide modulation and de-modulation functionality for data 704 that is communicated between the circuit 700 and an outside source. The outside source may include, for example, patient interface 50 as shown in FIG. 15.

In addition to data 704, power 710 may also be provided. The power 710 may be provided on the same signal line that carries the data 704. However, the power 710 may also be provided on a separate line that runs separate from the data line.

Alternatively, or in addition, to the modem 708, a multiplexor may be provided in order to combine multiple signals onto a single line. The signal wire 404 of the patient interface may be used to encode and decode data for reading sensors and operating controllers by adding a multiplexing circuit to modulate data for the controllers of the patient interface and demodulating signals from the sensor(s) of the patient interface device. A multiplexor 431 may be provided to multiplex the output of the amplifier 430 so that false temperature control or over temperature cut out does not occur. A multiplexor 433 may also be provided to multiplex power onto the signal wire 404. The multiplexor may also handle the de-multiplexing of an incoming signal into the original respective signals. A multiplexor may also be added to circuit configuration 700 to multiplex incoming signals from data 704 and the temperature reading from the NTC sensor 410.

Data 704 can include passive data. Such data, may include, for example the ambient air temperature within a patient interface or the amount of pressure and flow in the patient interface. Data 704 may additionally include commands. For example, the commands may include, an instruction that a particular sensor is to take a measurement or turn off/on, that an active vent on the patient interface is to be controlled, e.g., opened and/or closed or proportionally opened and/or proportionally closed to actively control respiratory pressure and flows. Circuit configuration 700 may provide an encoding feature that encodes data and/or commands before they are sent along the signal wire 404. Similarly, data and/or commands received by circuit configuration 700 may be decoded.

Circuit configuration 700 may also include functionality that facilitates the extraction of information from the received data. The PAP device 602 may further take a given action based on the extracted information. For example, a sensor may transmit that the humidity in the patient interface is above a certain threshold. Upon receiving this data, the PAP device, or humidifier, may take action to adjust the humidity in the patient interface.

Power Supply for Patient Interface System—Circuit for Patient Interface

Figure 28:
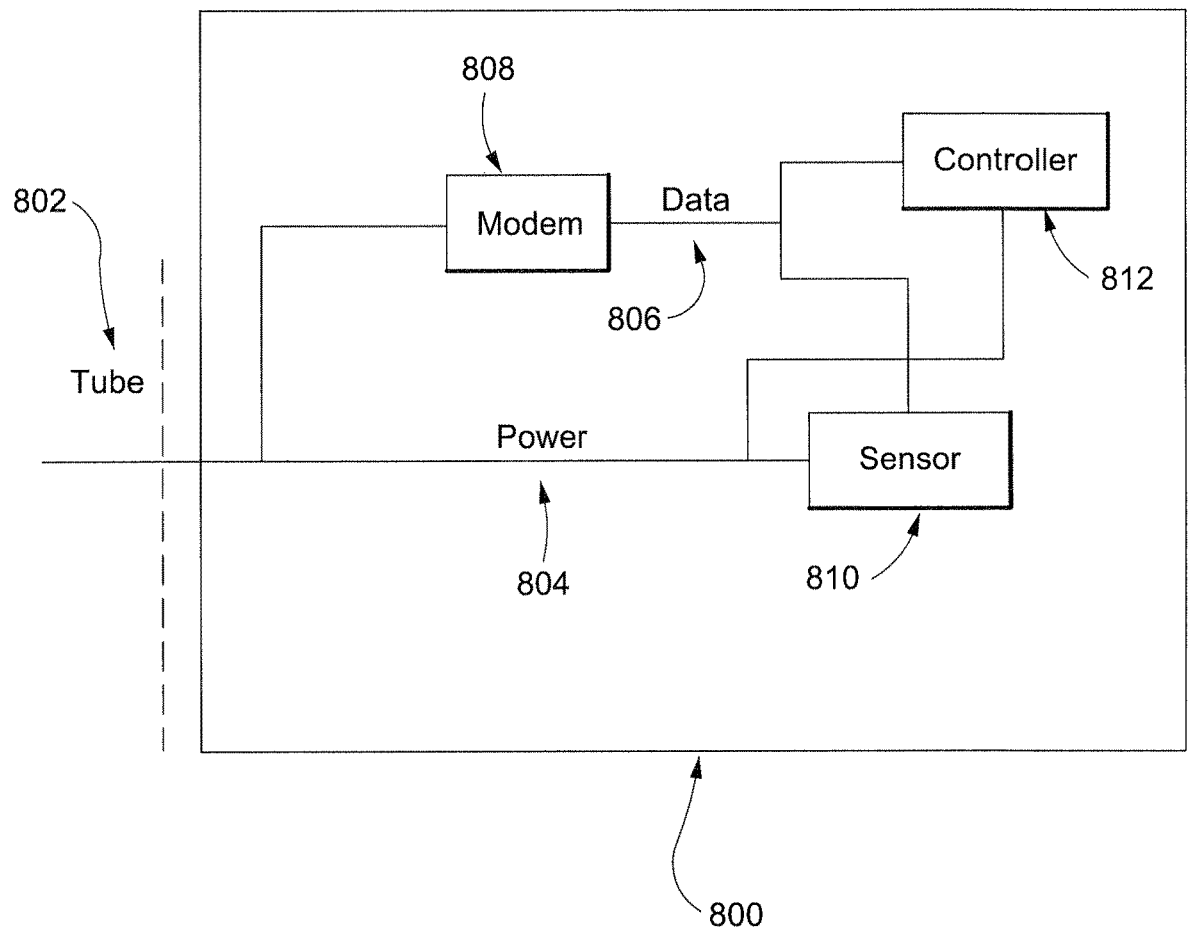
FIG. 28 schematically depicts a circuit in a patient interface device according to a further sample embodiment.

Referring to FIG. 28, a sample embodiment of a circuit associated with a patient interface that receives power and transfers data is shown. Circuit configuration 800 may be disposed at the patient interface end of tube 802, or may alternatively be disposed on the patient interface. In circuit configuration 800 both power 804 and data 806 are shown as being in communication with tube 802. In this sample embodiment, power and data are utilizing one signal wire. However, as explained above, other embodiments may utilize wires that are dedicated to power and data respectively.

Modem 808 provides modulation and demodulation functionality for data 806. Power 804 may be provided to sensor 810 and/or controller 812. Likewise, the data 806 may be provided to sensor 810 and/or controller 812. Thus, both the controllers and sensors can be linked up to the power and data provided from an outside source (e.g., a PAP device). Further, like circuit configuration 700, circuit configuration 800 may also include multiplexors and/or encoders to facilitate the transfer of data and power. In alternative embodiments, a microprocessor may be added to circuit configuration 800 to pre-condition signals, for example to compensate or calibrate raw sensor signals or to encode or compress data. Additional embodiments may utilize an isolation circuit for medical safety where wires cannot be applied to the circuits. For example, a transformer, capacitor or optical coupling may be used to electrically isolate the patient interface circuit for patient safety.

Sensor 810 may include, for example, sensors that detect temperature, humidity, flow and pressure, voice pattern or speech recognition, attitude detection (e.g., whether a patient is face down), breathing flow, gagging of the patient, oxygen saturation of the patient (e.g., a pulse oximeter), or particulates (e.g., for safety).

Controller 812 may include controllers that accomplish various tasks, for example, actuators that directly humidify the patient interface, an active vent, a speaker or alarm, a noise cancellation control, vibration control (e.g., to signal a patient to wakeup), etc.

The patient interface may also include light or optical sensing lamps. The patient interface may also be heated, e.g. a cushion or seal, to improve patient comfort. The patient interface heating may be controlled via the link. The patient interface may also include a controlled expansion foam or membrane seal that may use a variable force controlled via the link and patient interface circuit to improve the sealing of the patient interface with the face of the patient. Foam and/or seal characteristics may also be sensed to provide a patient interface seal "fit quality" and transmit data to the PAP device via the link. For example, the compression of the cushion or seal may be sensed by electrical resistance change and the data transmitted via the link to the PAP device to determine fit quality and/or permit patient interface control adjustment and/or sealing force to improve fit by improved compliance to patient facial contours.

Although the invention has been herein shown and described in what is conceived to be the most practical and preferred embodiments, it is recognized that departures can be made within the scope of the invention, which is not to be limited to the details described herein but is to embrace any and all equivalent assemblies, devices and apparatus. For example, the heating wires may be PTC elements with a voltage regulation to limit the temperature of the wires and/or the air in the tube(s). As another example, one or more PTC or NTC wires may be used in conjunction with a resistor to limit the temperature of the wires and the air. As a further example, NTC wires may be used with a current regulator, or a measure resistance, to limit the temperature of the heating wires. The temperature sensing and heating may also be performed using only two wires.

In this specification, the word "comprising" is to be understood in its "open" sense, that is, in the sense of "including", and thus not limited to its "closed" sense, that is the sense of "consisting only of". A corresponding meaning is to be attributed to the corresponding words "comprise," "comprised" and "comprises" where they appear.

It will further be understood that any reference herein to known prior art does not, unless the contrary indication appears, constitute an admission that such prior art is commonly known by those skilled in the art to which the invention relates.

What is claimed is:

1. A flow generator configured to pressurize a flow of breathable gas for delivery to a patient's airways, the flow generator comprising:
   a blower configured to pressurize the flow of breathable gas;
   a flow generator outlet in fluid communication with the blower and configured to receive an end of a breathable gas delivery tube, the flow generator outlet comprising electrical contacts configured to contact corresponding electrical terminals associated with the breathable gas delivery tube when the breathable gas delivery tube is received by the flow generator outlet; and
   a controller configured to receive signals from the breathable gas delivery tube by way of the electrical contacts of the flow generator outlet, the controller comprising a tube-type detect circuit and an over temperature protection circuit,
   wherein the tube-type detect circuit is configured so that when the breathable gas delivery tube is received by the flow generator outlet, the tube-type detect circuit determines the type of breathable gas delivery tube based on a signal from the electrical contacts of the flow generator outlet that is indicative of a condition of a resistor associated with the breathable gas delivery tube,
   wherein the over temperature protection circuit is configured to terminate power to the breathable gas delivery tube in response to the signal exceeding a threshold, and
   wherein the controller is configured to adjust the signal based on the type of breathable gas delivery tube detected by the controller so that the same over temperature protection circuit is operable with different types of breathable gas delivery tubes.

2. A flow generator according to claim 1, wherein the condition is a resistance of the resistor.

3. A flow generator according to claim 2, wherein the controller is configured to associate each type of breathable gas delivery tube with a unique resistor resistance.

4. A flow generator according to claim 1, wherein the condition is a voltage across the resistor.

5. A flow generator according to claim 4, wherein the type of breathable gas delivery tube connected to the flow generator is determined by comparing the voltage across the resistor to a reference voltage.

6. A flow generator according to claim 5, wherein the tube-type detect circuit comprises a plurality of reference voltages, and each type of breathable gas delivery tube is associated with a unique reference voltage.

7. A flow generator according to claim 1, wherein the controller is configured to adjust the performance of the flow generator based on the type of breathable gas delivery tube connected to the flow generator.

8. A flow generator according to claim 1, wherein the tube-type detect circuit is configured to detect more than two types of breathable gas delivery tubes.

9. A flow generator according to claim 1, wherein the controller further comprises a tube fault detection circuit configured to generate a tube fault signal when a voltage received from the breathable gas delivery tube is outside a reference voltage range.

10. A flow generator according to claim 9, wherein the controller is configured to terminate power to the breathable gas delivery tube when the tube fault detection circuit generates the tube fault signal.

11. A flow generator according to claim 1, wherein the tube-type detect circuit comprises a first comparator and the over temperature protection circuit comprises a second comparator, and wherein the controller is configured to amplify a signal sent to the second comparator based on a comparison made by the first comparator.

12. A flow generator according to claim 11, wherein the comparison made by the first comparator is between the signals received from the breathable gas delivery tube and a reference voltage.

13. A flow generator according to claim 12, wherein the controller is configured to amplify the signal sent to the second comparator when the signal received from the breathable gas delivery tube is equal to or greater than the reference voltage and is configured to send the signal to the second comparator without amplification when the signal received from the breathable gas delivery tube is less than the reference voltage.

14. A respiratory apparatus configured to deliver a flow of pressurized breathable gas to a patient's airways, the respiratory apparatus comprising:
    a breathable gas delivery tube comprising a resistor; and
    a flow generator, the flow generator comprising:
       a blower configured to pressurize the flow of breathable gas;
       a flow generator outlet in fluid communication with the blower and configured to receive an end of the breathable gas delivery tube, the flow generator outlet comprising electrical contacts configured to contact corresponding electrical terminals associated with the breathable gas delivery tube when the breathable gas delivery tube is received by the flow generator outlet; and
       a controller configured to receive signals from the breathable gas delivery tube by way of the electrical contacts of the flow generator outlet, the controller comprising a tube-type detect circuit and an over temperature protection circuit,
       wherein the tube-type detect circuit is configured so that when the breathable gas delivery tube is received by the flow generator outlet, the tube-type detect circuit determines the type of breathable gas delivery tube based on a signal from the electrical contacts of the flow generator outlet that is indicative of a condition of the resistor associated with the breathable gas delivery tube,
       wherein the over temperature protection circuit is configured to terminate power to the breathable gas delivery tube in response to the signal exceeding a threshold, and
       wherein the controller is configured to adjust the signal based on the type of breathable gas delivery tube detected by the controller so that the same over temperature protection circuit is operable with different types of breathable gas delivery tubes.

15. A respiratory apparatus according to claim 14, wherein the resistor is a thermistor.

16. A respiratory apparatus according to claim 15, wherein the breathable gas delivery tube further comprises a heater.

17. A respiratory apparatus according to claim 16, wherein the controller is configured to disable the heater in response to a fault detected in the thermistor.

18. A respiratory apparatus according to claim 17, wherein the fault is an open circuit or a short circuit.

19. A respiratory apparatus according to claim 14, wherein the tube-type detect circuit is configured to distinguish between diameters of the different types of breathable gas delivery tubes.

20. A respiratory apparatus according to claim 14, further comprising a patient interface connected to the breathable gas delivery tube and configured to sealingly engage the patient's face.

\* \* \* \* \*